(12) United States Patent
Guo et al.

(10) Patent No.: US 7,754,678 B2
(45) Date of Patent: Jul. 13, 2010

(54) MEMBRANE PENETRATING PEPTIDES AND USES THEREOF

(75) Inventors: Yong Guo, Fresh Meadows, NY (US); Clarence C Morse, Asbury, NJ (US); Zhengbin Yao, Sugar Land, TX (US); George Keesler, Somerville, NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 11/251,734

(22) Filed: Oct. 17, 2005

(65) Prior Publication Data

US 2006/0100134 A1 May 11, 2006

Related U.S. Application Data

(63) Continuation of application No. 09/933,780, filed on Aug. 21, 2001, now abandoned.

(60) Provisional application No. 60/227,647, filed on Aug. 25, 2000.

(30) Foreign Application Priority Data

Feb. 7, 2001 (GB) ................................. 0103110.3

(51) Int. Cl.
*A61K 38/00* (2006.01)
*C07K 14/00* (2006.01)
(52) U.S. Cl. .......................................... 514/2; 530/300
(58) Field of Classification Search ........................ None
See application file for complete search history.

(56) References Cited

U.S. PATENT DOCUMENTS

| | | | |
|---|---|---|---|
| 5,652,122 A | 7/1997 | Frankel et al. | |
| 5,670,617 A | 9/1997 | Frankel et al. | |
| 5,674,980 A | 10/1997 | Frankel et al. | |
| 5,747,641 A | 5/1998 | Frankel et al. | |
| 5,766,903 A | 6/1998 | Sarnow et al. | |
| 5,804,604 A | 9/1998 | Frankel et al. | |
| 5,843,643 A * | 12/1998 | Ratner | 435/6 |
| 5,877,282 A | 3/1999 | Nadler et al. | |
| 5,929,042 A | 7/1999 | Troy et al. | |
| 6,197,925 B1 * | 3/2001 | Crabtree et al. | 530/300 |
| 6,217,912 B1 | 4/2001 | Park et al. | |
| 6,235,521 B1 | 5/2001 | Nakanishi et al. | |
| 6,248,558 B1 | 6/2001 | Lin et al. | |
| 6,258,774 B1 | 7/2001 | Stein et al. | |
| 6,316,003 B1 | 11/2001 | Frankel et al. | |
| 6,436,628 B1 * | 8/2002 | Young et al. | 435/4 |
| 6,555,328 B1 * | 4/2003 | Keesler et al. | 435/15 |
| 2004/0002455 A1 * | 1/2004 | Uger et al. | 514/12 |
| 2006/0002946 A1 * | 1/2006 | Gallichan et al. | 424/185.1 |

FOREIGN PATENT DOCUMENTS

| | | |
|---|---|---|
| WO | WO 98/49325 | 11/1998 |
| WO | WO 99/07728 | 2/1999 |
| WO | WO 99/49060 | 9/1999 |
| WO | WO 99/57138 | 11/1999 |
| WO | WO 00/32236 | 6/2000 |
| WO | WO 00/32237 | 6/2000 |
| WO | WO 01/38547 | 5/2001 |
| WO | WO 01/93836 | 12/2001 |

OTHER PUBLICATIONS

Takumi et al., "A mammalian ortholog of Drosophila timeless, highly expressed in SCN and retina, forms a complex with mPER1", Genes to Cells 4: 67-75 (1999).*
Vielhaber et al., "Nuclear entry of the circadian regulator mPER1 is controlled by mammalian casein kinase I ϵ", Molecular and Cellular Biology 20(13): 4888-4899 (Jul. 2000).*
D.J. Mitchell et al., Polyarginine Enters Cells More Efficiently Than Other Polycationic Homopolymers, Journal of Peptide Research, vol. 56, No. 5, Nov. 2000, pp. 318-325.
E. Vives et al., A Truncated HIV-1 TAT Protein Basic Domain Rapidly Translocates Through The Plasma Membrane and Accumulates in the Cell Nucleus, Journ. of Biological Chemistry, vol. 22, No. 25, Jun. 20, 1997, pp. 16010-16017.
J.L. Pinkham et al., Sequence and Nuclear Localization of the *Saccharomyces cerevisiae* HAP2 Protein, a Transcriptional Activator, Molecular and Cellular Biology, Feb. 1987, vol. 7, No. 2, pp. 578-585.
M. Lindgren et al., Cell-Penetrating Peptides, Trends in Pharmacological Sciences, Elsevier Trends Journal, vol. 21, No. 3, Mar. 2000, pp. 99-103.
S. Futaki et al., Arginine-rich Peptides, Journal of Biological Chemistry, vol. 276, No. 8, Nov. 17, 2000, pp. 5836-5840.
S. Schwarze et al., In Vivo Protein Transduction: Delivery of a Biologically Active Protein into the Mouse, Science, vol. 285, Sep. 3, 1999, pp. 1569-1572.
Yagita et al., Dimerization and nuclear entry of mPER proteins in mammalian cells, Genes and Development, vol. 1. No. 11, Jun. 1, 2000, pp. 1353-1363.

* cited by examiner

*Primary Examiner*—Anand U Desai

(57) ABSTRACT

The present invention is directed to membrane penetrating peptides useful as in vivo, ex vivo and in vitro intracellular delivery devices for compound of interest. More particularly, the invention involves identification of membrane penetrating peptides which may be used as protein carriers for delivery of a compound of interest to cells, to methods of delivering a compound of interest attached to membrane penetrating peptides to cells.

12 Claims, 8 Drawing Sheets

Figure 1A

SEQUENCE LISTING

<160> NUMBER OF SEQ ID NOS: 56

<210> SEQ ID NO 1
<211> LENGTH: 10
<212> TYPE: PRT
<213> ORGANISM: Artificial Sequence
<220> FEATURE:
<223> OTHER INFORMATION: Sequence of nuclear location sequence contained
      within the N-terminal of IL-alpha propiece.

<400> SEQUENCE: 1

Asn Gly Lys Val Leu Lys Lys Arg Arg Leu
1               5                   10

<210> SEQ ID NO 2
<211> LENGTH: 16
<212> TYPE: PRT
<213> ORGANISM: Artificial Sequence
<220> FEATURE:
<223> OTHER INFORMATION: Signal sequence peptide from Antennapedia
      homeodomain

<400> SEQUENCE: 2

Arg Gln Ile Lys Ile Trp Phe Gln Asn Arg Arg Met Lys Trp Lys Lys
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Fibroblast growth factor signal sequence
      peptide

<400> SEQUENCE: 3

Ala Ala Val Ala Leu Leu Pro Ala Val Leu Leu Ala Leu Leu Ala
1               5                   10                  15

<210> SEQ ID NO 4
<211> LENGTH: 29
<212> TYPE: PRT
<213> ORGANISM: Artificial Sequence
<220> FEATURE:
<223> OTHER INFORMATION: HIV tat signal sequence peptide

<400> SEQUENCE: 4

Cys Phe Ile Thr Lys Ala Leu Gly Ile Ser Tyr Gly Arg Lys Lys Arg
1               5                   10                  15

Arg Gln Arg Arg Arg Pro Pro Gln Gly Ser Gln Thr His
            20                  25

<210> SEQ ID NO 5
<211> LENGTH: 4
<212> TYPE: PRT
<213> ORGANISM: Artificial Sequence
<220> FEATURE:
<223> OTHER INFORMATION: Peptide sequence of an N-terminal fluorescein
      isothiocyanate (FITC) peptide motif

<400> SEQUENCE: 5

Gly Gly Gly Gly
1

<210> SEQ ID NO 6
<211> LENGTH: 7

```
<212> TYPE: PRT
<213> ORGANISM: Artificial Sequence
<220> FEATURE:
<223> OTHER INFORMATION: Fragment of IFN-gamma

<400> SEQUENCE: 6

Arg Lys Arg Lys Arg Ser Arg
1               5

<210> SEQ ID NO 7
<211> LENGTH: 7
<212> TYPE: PRT
<213> ORGANISM: Artificial Sequence
<220> FEATURE:
<223> OTHER INFORMATION: Fragment of the N-terminus of fibroblast growth
      factor.

<400> SEQUENCE: 7

Asn Tyr Lys Lys Pro Lys Leu
1               5

<210> SEQ ID NO 8
<211> LENGTH: 8
<212> TYPE: PRT
<213> ORGANISM: Artificial Sequence
<220> FEATURE:
<223> OTHER INFORMATION: Luinus luteus nuclear protein import sequence

<400> SEQUENCE: 8

Lys Pro Lys Lys Lys Lys Glu Lys
1               5

<210> SEQ ID NO 9
<211> LENGTH: 5
<212> TYPE: PRT
<213> ORGANISM: Artificial Sequence
<220> FEATURE:
<223> OTHER INFORMATION: Sequence of the basic motif in the nuclear
      protein import sequence of Smad 3 protein

<400> SEQUENCE: 9

Lys Lys Leu Lys Lys
1               5

<210> SEQ ID NO 10
<211> LENGTH: 11
<212> TYPE: PRT
<213> ORGANISM: Artificial Sequence
<220> FEATURE:
<223> OTHER INFORMATION: Sequence of intracellular loop of 5HT2A
      receptor

<400> SEQUENCE: 10

Ser Leu Glu Lys Lys Leu Gln Asn Ala Thr Asn
1               5                   10

<210> SEQ ID NO 11
<211> LENGTH: 23
<212> TYPE: PRT
<213> ORGANISM: Artificial Sequence
<220> FEATURE:
<223> OTHER INFORMATION: Sequence of C-terminal transmembrane 7 domain
      derived from 5HT2A receptor

<400> SEQUENCE: 11

Lys Thr Tyr Arg Ser Ala Phe Ser Arg Tyr Ile Gln Tyr Lys Glu Asn
1               5                   10                  15
```

```
Lys Lys Pro Leu Gln Leu Ile
            20

<210> SEQ ID NO 12
<211> LENGTH: 9
<212> TYPE: PRT
<213> ORGANISM: Artificial Sequence
<220> FEATURE:
<223> OTHER INFORMATION: Fragment of HIV TAT

<400> SEQUENCE: 12

Arg Lys Lys Arg Arg Gln Arg Arg Arg
1               5

<210> SEQ ID NO 13
<211> LENGTH: 4
<212> TYPE: PRT
<213> ORGANISM: Artificial Sequence
<220> FEATURE:
<223> OTHER INFORMATION: Synthetic peptide

<400> SEQUENCE: 13

Gly Phe Leu Gly
1

<210> SEQ ID NO 14
<211> LENGTH: 5
<212> TYPE: PRT
<213> ORGANISM: Artificial Sequence
<220> FEATURE:
<223> OTHER INFORMATION: Synthetic peptide

<400> SEQUENCE: 14

Asp Asp Asp Asp Lys
1               5

<210> SEQ ID NO 15
<211> LENGTH: 4
<212> TYPE: PRT
<213> ORGANISM: Artificial Sequence
<220> FEATURE:
<223> OTHER INFORMATION: synthetic peptide

<400> SEQUENCE: 15

Glu Tyr Phe Pro
1

<210> SEQ ID NO 16
<211> LENGTH: 16
<212> TYPE: PRT
<213> ORGANISM: Artificial Sequence
<220> FEATURE:
<223> OTHER INFORMATION: Nuclear protein import sequence of hPER1

<400> SEQUENCE: 16

Ser Arg Arg His His Cys Arg Ser Lys Ala Lys Arg Ser Arg His His
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 17

Gly Arg Arg His His Cys Arg Ser Lys Ala Lys Arg Ser Arg His His
```

<210> SEQ ID NO 18
<211> LENGTH: 23
<212> TYPE: PRT
<213> ORGANISM: Artificial Sequence
<220> FEATURE:
<223> OTHER INFORMATION: Synthetic peptide

<400> SEQUENCE: 18

Gly Met Asp Tyr Lys Asp Asp Asp Lys Gly Tyr Gly Arg Lys Lys
1               5                   10                  15

Lys Arg Arg Gln Arg Arg Arg
            20

<210> SEQ ID NO 19
<211> LENGTH: 23
<212> TYPE: PRT
<213> ORGANISM: Artificial Sequence
<220> FEATURE:
<223> OTHER INFORMATION: Synthetic peptide

<400> SEQUENCE: 19

Gly Met Asp Tyr Lys Asp Asp Asp Lys Gly Tyr Gly Arg Lys Lys
1               5                   10                  15

Lys Arg Arg Gln Arg Arg Arg
            20

<210> SEQ ID NO 20
<211> LENGTH: 19
<212> TYPE: PRT
<213> ORGANISM: Artificial Sequence
<220> FEATURE:
<223> OTHER INFORMATION: Synthetic peptide

<400> SEQUENCE: 20

Gly Met Asp Tyr Lys Asp Asp Asp Lys Gly Met Asp Tyr Asp Asp
1               5                   10                  15

Asp Asp Lys

<210> SEQ ID NO 21
<211> LENGTH: 17
<212> TYPE: PRT
<213> ORGANISM: Artificial Sequence
<220> FEATURE:
<223> OTHER INFORMATION: Synthetic peptide

<400> SEQUENCE: 21

Gly Arg Gln Ile Lys Ile Trp Phe Gln Asn Arg Arg Met Lys Trp Lys
1               5                   10                  15

Lys

<210> SEQ ID NO 22
<211> LENGTH: 10
<212> TYPE: PRT
<213> ORGANISM: Artificial Sequence
<220> FEATURE:
<223> OTHER INFORMATION: Synthetic peptide

<400> SEQUENCE: 22

Gly Arg Arg Arg Arg Arg Arg Arg Arg Arg
1               5                   10

<210> SEQ ID NO 23

```
<211> LENGTH: 10
<212> TYPE: PRT
<213> ORGANISM: Artificial Sequence
<220> FEATURE:
<223> OTHER INFORMATION: Synthetic peptide

<400> SEQUENCE: 23

Gly Lys Lys Lys Lys Lys Lys Lys Lys Lys
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthetic peptide

<400> SEQUENCE: 24

Gly His His His His His His His His His
1               5                   10

<210> SEQ ID NO 25
<211> LENGTH: 9
<212> TYPE: PRT
<213> ORGANISM: Artificial Sequence
<220> FEATURE:
<223> OTHER INFORMATION: Synthetic peptide

<400> SEQUENCE: 25

Gly Asp Pro Lys Lys Lys Arg Lys Val
1               5

<210> SEQ ID NO 26
<211> LENGTH: 19
<212> TYPE: PRT
<213> ORGANISM: Artificial Sequence
<220> FEATURE:
<223> OTHER INFORMATION: Synthetic peptide

<400> SEQUENCE: 26

Gly Lys Lys Thr Gly Lys Asn Arg Lys Leu Lys Ser Lys Arg Val Lys
1               5                   10                  15

Pro Arg Asp

<210> SEQ ID NO 27
<211> LENGTH: 12
<212> TYPE: PRT
<213> ORGANISM: Artificial Sequence
<220> FEATURE:
<223> OTHER INFORMATION: Synthetic peptide

<400> SEQUENCE: 27

Gly Arg Lys Gly Lys His Lys Arg Lys Lys Leu Pro
1               5                   10

<210> SEQ ID NO 28
<211> LENGTH: 18
<212> TYPE: PRT
<213> ORGANISM: Artificial Sequence
<220> FEATURE:
<223> OTHER INFORMATION: Synthetic peptide

<400> SEQUENCE: 28

Gly Lys Arg Val Ala Lys Arg Lys Leu Ile Glu Gln Asn Arg Glu Arg
1               5                   10                  15

Arg Arg
```

```
<210> SEQ ID NO 29
<211> LENGTH: 18
<212> TYPE: PRT
<213> ORGANISM: Artificial Sequence
<220> FEATURE:
<223> OTHER INFORMATION: Synthetic peptide

<400> SEQUENCE: 29

Gly Arg Lys Leu Lys Lys Lys Asn Glu Lys Glu Asp Lys Arg Pro
1               5                   10                  15

Arg Thr

<210> SEQ ID NO 30
<211> LENGTH: 17
<212> TYPE: PRT
<213> ORGANISM: Artificial Sequence
<220> FEATURE:
<223> OTHER INFORMATION: synthetic peptide

<400> SEQUENCE: 30

Gly Lys Lys Thr Asn Leu Phe Ser Ala Leu Ile Lys Lys Lys Thr
1               5                   10                  15

Ala

<210> SEQ ID NO 31
<211> LENGTH: 18
<212> TYPE: PRT
<213> ORGANISM: Artificial Sequence
<220> FEATURE:
<223> OTHER INFORMATION: Synthetic peptide

<400> SEQUENCE: 31

Gly Arg Arg Glu Arg Asn Lys Met Ala Ala Ala Lys Cys Arg Asn Arg
1               5                   10                  15

Arg Arg

<210> SEQ ID NO 32
<211> LENGTH: 18
<212> TYPE: PRT
<213> ORGANISM: Artificial Sequence
<220> FEATURE:
<223> OTHER INFORMATION: Synthetic peptide

<400> SEQUENCE: 32

Gly Lys Arg Ala Arg Asn Thr Glu Ala Ala Arg Arg Ser Arg Ala Arg
1               5                   10                  15

Lys Leu

<210> SEQ ID NO 33
<211> LENGTH: 14
<212> TYPE: PRT
<213> ORGANISM: Artificial Sequence
<220> FEATURE:
<223> OTHER INFORMATION: Synthetic peptide

<400> SEQUENCE: 33

Gly Arg Arg Arg Arg Ala Thr Ala Lys Tyr Arg Thr Ala His
1               5                   10

<210> SEQ ID NO 34
<211> LENGTH: 15
<212> TYPE: PRT
<213> ORGANISM: Artificial Sequence
```

```
<220> FEATURE:
<223> OTHER INFORMATION: Synthetic peptide

<400> SEQUENCE: 34

Gly Lys Arg Arg Arg Arg Ala Thr Ala Lys Tyr Arg Ser Ala His
1               5                   10                  15

<210> SEQ ID NO 35
<211> LENGTH: 12
<212> TYPE: PRT
<213> ORGANISM: Artificial Sequence
<220> FEATURE:
<223> OTHER INFORMATION: Synthetic peptide

<400> SEQUENCE: 35

Gly Arg Arg Arg Arg Lys Arg Leu Ser His Arg Thr
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Synthetic peptide

<400> SEQUENCE: 36

Gly Arg Arg Arg Arg Arg Glu Arg Asn Lys
1               5                   10

<210> SEQ ID NO 37
<211> LENGTH: 16
<212> TYPE: PRT
<213> ORGANISM: Artificial Sequence
<220> FEATURE:
<223> OTHER INFORMATION: Synthetic peptide

<400> SEQUENCE: 37

Gly Lys His Arg His Glu Arg Gly His His Arg Asp Arg Arg Glu Arg
1               5                   10                  15

<210> SEQ ID NO 38
<211> LENGTH: 17
<212> TYPE: PRT
<213> ORGANISM: Artificial Sequence
<220> FEATURE:
<223> OTHER INFORMATION: Synthetic peptide

<400> SEQUENCE: 38

Gly Lys Lys Lys Arg Lys Leu Ser Asn Arg Glu Ser Ala Lys Arg Ser
1               5                   10                  15

Arg

<210> SEQ ID NO 39
<211> LENGTH: 16
<212> TYPE: PRT
<213> ORGANISM: Artificial Sequence
<220> FEATURE:
<223> OTHER INFORMATION: Synthetic peptide

<400> SEQUENCE: 39

Ser Arg Arg His His Cys Arg Ser Lys Ala Lys Arg Ser Arg His His
1               5                   10                  15

<210> SEQ ID NO 40
<211> LENGTH: 16
<212> TYPE: PRT
```

<213> ORGANISM: Artificial Sequence
<220> FEATURE:
<223> OTHER INFORMATION: Synthetic peptide

<400> SEQUENCE: 40

Ser Ala Arg His His Cys Arg Ser Lys Ala Lys Arg Ser Arg His His
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Synthetic peptide

<400> SEQUENCE: 41

Ser Arg Ala His His Cys Arg Ser Lys Ala Lys Arg Ser Arg His His
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Synthetic peptide

<400> SEQUENCE: 42

Ser Arg Arg Ala His Cys Arg Ser Lys Ala Lys Arg Ser Arg His His
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: Synthetic peptide

<400> SEQUENCE: 43

Ser Arg Arg His Ala Cys Arg Ser Lys Ala Lys Arg Ser Arg His His
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Synthetic peptide

<400> SEQUENCE: 44

Ser Arg Arg His His Ala Arg Ser Lys Ala Lys Arg Ser Arg His His
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Synthetic peptide

<400> SEQUENCE: 45

Ser Arg Arg His His Cys Ala Ser Lys Ala Lys Arg Ser Arg His His
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: Synthetic peptide

<400> SEQUENCE: 46

Ser Arg Arg His His Cys Arg Ala Lys Ala Lys Arg Ser Arg His His
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Synthetic peptide

<400> SEQUENCE: 47

Ser Arg Arg His His Cys Arg Ser Ala Ala Lys Arg Ser Arg His His
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: Synthetic peptide

<400> SEQUENCE: 48

Ser Arg Arg His His Cys Arg Ser Lys Ala Ala Arg Ser Arg His His
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Synthetic peptide

<400> SEQUENCE: 49

Ser Arg Arg His His Cys Arg Ser Ala Lys Ala Ser Arg Ser Arg His His
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Synthetic peptide

<400> SEQUENCE: 50

Ser Arg Arg His His Cys Arg Ser Lys Ala Lys Arg Ala Arg His His
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Synthetic peptide

<400> SEQUENCE: 51

Ser Arg Arg His His Cys Arg Ser Lys Ala Lys Arg Ser Ala His His
1               5                   10                  15

<210> SEQ ID NO 52
<211> LENGTH: 13
<212> TYPE: PRT
<213> ORGANISM: Artificial Sequence
<220> FEATURE:

-continued

<223> OTHER INFORMATION: Synthetic peptide

<400> SEQUENCE: 52

Arg Arg His His Cys Arg Ser Lys Ala Lys Arg Ser Arg
1               5                   10

<210> SEQ ID NO 53
<211> LENGTH: 15
<212> TYPE: PRT
<213> ORGANISM: Artificial Sequence
<220> FEATURE:
<223> OTHER INFORMATION: Synthetic peptide

<400> SEQUENCE: 53

Gln Glu Leu Ser Glu Gln Ile His Arg Leu Leu Leu Gln Pro Val
1               5                   10                  15

<210> SEQ ID NO 54
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: X = R, H or K
<220> FEATURE:
<221> NAME/KEY: misc_feature
<222> LOCATION: (1)..(4)
<223> OTHER INFORMATION: X = R, H or K

<400> SEQUENCE: 54

Xaa Xaa Xaa Xaa
1

<210> SEQ ID NO 55
<211> LENGTH: 11
<212> TYPE: PRT
<213> ORGANISM: Artificial Sequence
<220> FEATURE:
<223> OTHER INFORMATION: Synthetic peptide

<400> SEQUENCE: 55

Arg Lys Gly Lys His Lys Arg Lys Lys Leu Pro
1               5                   10

<210> SEQ ID NO 56
<211> LENGTH: 15
<212> TYPE: PRT
<213> ORGANISM: Artificial Sequence
<220> FEATURE:
<223> OTHER INFORMATION: Nuclear protein import sequence of hPER1

<400> SEQUENCE: 56

Arg Arg His His Cys Arg Ser Lys Ala Lys Arg Ser Arg His His
1               5                   10                  15

MEMBRANE PENETRATING PEPTIDES AND USES THEREOF

This application claims the benefit of U.S. Provisional Application No. 60/227,647, filed Aug. 25, 2001 and GB Application 0103110.3, filed Feb. 7, 2001.

FIELD OF THE INVENTION

The invention relates to membrane penetrating peptides useful as in vitro, ex vivo and in vivo delivery devices for intracellular delivery of a compound of interest to cells in vitro, ex vivo and in vivo, compositions comprising the same and methods of using the same. The invention also includes identification of additional membrane penetrating peptides useful as delivery devices for intracellular delivery of a compound of interest to cells in vitro, ex vivo and in vivo.

BACKGROUND OF THE INVENTION

The delivery of small molecules, oligonucleotides, and proteins through biological membranes is a major challenge facing therapy and validation paradigms. It has recently been established that transducing peptides derived from Antennapedia, TAT-HIV, and VP22 can penetrate biological membranes, act as cargo vehicles, and target to specific subcellular compartments. Here we show the identification of a nuclear localization sequence (NLS) within human Period 1 (hPER1) circadian protein that functions as a transducing peptide. More importantly, using database mining, we have uncovered additional transducing peptides embedded within the NLS's of other proteins and extend the number of gene-encoded transducing peptides from 3 to 14. Our data suggest that transducing peptides are found within NLS's and are prevalent, diverse, and distributed widely throughout the genome. It is well established that certain extracellular and intracellular proteins are targeted to specific organelles within a cell, transmembrane or secreted from the cell. The biological mechanisms by which intracellular protein targeting occurs continues to be characterized, but is well recognized that one mechanism for localization occurs by virtue of specific leader sequence contained within the protein of interest, or intraprotein sequence. Localization of proteins within selected cellular organelles is aided by specific targeting sequences. A number of nuclear localization sequences (NLSS) have been identified in proteins that permit the protein to be transported or otherwise pass from the cytoplasm into the nuclear membrane.

Fusion proteins containing the targeting sequence and another, otherwise non-targeted protein, are localized in the selected cellular organelle depending on the targeting sequence selected. For example, Ferullo, J. M. and Paget, E. FR 279695, disclose selective compartmentalization of an hydroxyphenylpyruvate dioxygenase (HPPD) fused to a signal sequence directing the enzyme to a cellular compartment other than the cytosol, e.g., a vacuole. Similarly, WO 0147950 (Wehrle-Haller, Bernhard M.; Imhof, Beat A) identify a new determinant responsible for basolateral targeting and prolonged exposure of cell-surface-anchored growth factors at cell surfaces. The signal is a mono-leucine dependent basolateral sorting signal consisting of the amino acid sequence X1h2X3h4Lp5p6, wherein: X1 represents a polar amino acid residue or alanine, h2 represents any hydrophobic amino acid residue, X3 represents any amino acid residue, h4 represents any hydrophobic amino acid residue, except leucine and isoleucine, L represents a leucine residue, p5 represents any polar amino acid residue, and p6 represents any polar amino acid. Richardson, A. E., et al., $Plant\ J.$ (2001), 25(6), 641-649 describe manipulation of the enzyme aspergillus phytase to include the signal peptide sequence from the carrot extensin gene. The resulting fusion protein was only effective when secreted as an extracellular enzyme into the adjacent soil, and resulted in a 20-fold increase in total root phytase activity in transgenic lines and subsequent improved phosphorus nutrition, such that the growth and phosphorus content of the plants was equivalent to control plants supplied with inorganic phosphate. WO 0132894 (Lok, S.) disclose use of the signal anchor domain sequences of type II cell surface proteins to anchor recombinant proteins into surface of transfected cells. A characteristic feature of type II cell surface proteins is that they are held within the cellular membrane by a single hydrophobic transmembrane domain and are oriented with their C-terminus outside the cell.

More recently, a few proteins have been identified which are capable of passing through the cellular membrane without requiring active transport mechanisms or 'pores'. It is recently established that membrane penetrating peptides (MPPs, also known as protein transduction domain, "PTD") derived from Antennapedia, TAT, and VP22 can penetrate biological membranes and target to specific subcellular compartments. None of these previously disclosed proteins are derived from mammalian proteins. The present invention is directed to the discovery that polypeptides derived from mammalian or yeast proteins nuclear localization sequences (NLSs) or overlapping with NLS's are capable of acting as MPPs, and identification of a specific polypeptide sequences capable of penetrating cellular membranes, even when conjugated to large proteins, such as biologically active proteins, or other organic compounds.

Nuclear transport is essential to a number of biological processes including gene expression and cell division, as well as to viral replication, tumorigenesis and tumor cell proliferation. The mechanism of nuclear transport has only recently been characterized in detail and has been shown to involve a number of discrete steps. Proteins that are destined to be transported into the nucleus contain within their amino acid sequence a short stretch of amino acids termed a nuclear localization sequence ("NLS"). These sequences may occur anywhere within the amino acid sequence and are typically four to about eight amino acids. These sequences are generally basic (i.e., positively charged) in nature, however, there has been no consensus sequence identified. Thus, there is a wide variety of these sequences that appear to be specific for particular proteins.

Within the cell, these NLSs may be either masked or unmasked by accessory proteins or by conformational changes within the NLS-containing protein. An NLS may be masked because it is buried in the core of the protein and not exposed on the surface of the protein. Unmasking of NLSs, and nuclear translocation of cytoplasmic proteins may be triggered by phosphorylation, dephosphorylation, proteolytic digestion, subunit association or dissociation of an inhibitory subunit, or the like. Accordingly, the masking and unmasking of NLSs provides a mechanism by which the transport of these cytoplasmic proteins into the nucleus may be regulated. For example, the transcription factor NF-AT contains nuclear localization sequences which allow NF-AT to translocate to the nucleus in the presence of intracellular calcium, but which are shielded by forming intramolecular associations with other domains in the NF-AT polypeptide in the absence of calcium.

Lee, H. C. and Bernstein, H. D. $Proc.\ Natl.\ Acad.\ Sci.\ U.S.A.$ (2001), 98(6), 3471-3476 studied the mechanism involved for presecretory proteins such as maltose binding protein (MBP) and outer membrane protein A (OmpA) that are targeted to the *E. coli* inner membrane by the molecular chaperone SecB, in contrast to the targeting of integral membrane proteins by the signal recognition particle (SRP). The authors found that replacement of the MBP or OmpA signal peptide with the first transmembrane segment of AcrB abolished the dependence on SecB for transport and rerouted both proteins into the SRP targeting pathway.

Some proteins contain cytoplasmic localization sequences (CLS), or nuclear export sequences, which ensure the protein remains predominantly in the cytoplasm. For example, Hamilton, M. H. et al., *J. Biol. Chem.* (2001), 276(28), 26324-26331 demonstrate that the ubiquitin-protein ligase (E3), hRPF1/Nedd4, a component of the ubiquitin-proteasome pathway responsible for substrate recognition and specificity, is capable of entering the nucleus, but the presence of a functional Rev-like nuclear export sequence in hRPF1/Nedd4 ensures a predominant cytoplasmic localization. The cytoplasmic domains of many membrane proteins contain sorting signals that mediate their endocytosis from the plasma membrane.

Heineman, T. C. and Hall, S. L. *Virology* (2001), 285(1), 42-49 studied three consensus internalization motifs within the cytoplasmic domain of VZV gB and determined that internalization of VZV gB, and its subsequent localization to the Golgi, is mediated by two tyrosine-based sequence motifs in its cytoplasmic domain. In mammalian cells and yeasts, amino acid motifs in the cytoplasmic tails of transmembrane proteins play a prominent role in protein targeting in the early secretory pathway by mediating localization to or rapid export from the endoplasmic reticulum (ER). Hoppe, H. C. and Joiner, K. A. *Cell. Microbiol.* (2000), 2(6), 569-578.

The mammalian endopeptidase, furin, is predominantly localized to the trans-Golgi network (TGN) at steady state. The localization of furin to this compartment seems to be the result of a dynamic process in which the protein undergoes cycling between the TGN and the plasma membrane. Both TGN localization and internalization from the plasma membrane are mediated by targeting information contained within the cytoplasmic domain of furin. Voorhees, P., et al., *EMBO J.* (1995), 14(20), 4961-75 report that there are at least two cytoplasmic determinants that contribute to the steady-state localization and trafficking of furin. The first determinant corresponds to a canonical tyrosine-based motif, YKGL (residues 758-761), that functions mainly as an internalization signal. The second determinant consists of a strongly hydrophilic sequence (residues 766-783) that contains a large cluster of acidic residues (E and D) and is devoid of any tyrosine-based or di-leucine-based motifs. This second determinant is capable of conferring localization to the TGN as well as mediating internalization from the plasma membrane.

The trans-Golgi network (TGN) plays a central role in protein sorting/targeting and the sequence SXYQRL can by itself confer significant TGN localization. Wong, S. H., and Hong, W. *J. Biol. Chem.* (1993), 268(30), 22853-62 report detailed mutagenesis of the 32-residue sequence of TGN38, an integral membrane protein confined mainly to the TGN, and determined that the Ser, Tyr, and Leu residues at positions 23, 25, and 28, respectively, are essential for TGN localization. When the cytoplasmic 32-residue sequence of TGN38 was fused to the ecto- and transmembrane domains of glycophorin A (a surface protein), the resulting chimeric protein was localized to the TGN.

It is well recognized that certain proteins are either only active in a specific organelle, or are capable of different functions depending on their localization. For example, appropriate subcellular localization is crucial for regulation of NF-κB function. Huang, T. T., et al., *Proc. Natl. Acad. Sci. U.S.A.* (2000), 97(3), 1014-1019, show that latent NF-κB complexes can enter and exit the nucleus in preinduction states and identified a previously uncharacterized nuclear export sequence in residues 45-54 of IκBα that was required for cytoplasmic localization of inactive complexes. It appears that NF-κB/IκBα complexes shuttle between the cytoplasm and nucleus by a nuclear localization signal-dependent nuclear import and a CRM1-dependent nuclear export and that the dominant nuclear export over nuclear import contributes to the largely cytoplasmic localization of the inactive complexes to achieve efficient NF-κB activation by extracellular signals.

Nuclear import of classical nuclear localization sequence-containing proteins involves the assembly of an import complex at the cytoplasmic face of the nuclear pore complex (NPC) followed by movement of this complex through the NPC and release of the import substrate into the nuclear interior. In combination with Ran, two other soluble factors are thought to be absolutely required to mediate the nuclear import of a protein containing a classical or basic NLS into the nucleus. The first is karyopherin/importin α (Kap α), which binds a classical NLS and then forms a complex with karyopherin/importin β1 (Kapp β1). Adam, S. A., and Gerace, L. (1991) *Cell* 66, 837-847; Görlich, D., et al. (1994) *Cell* 79, 767-778; Moroianu, J., et al. (1995) *Proc. Natl. Acad. Sci. U.S.A.* 92, 2008-2011; Radu, A., et al. (1995) *Proc. Natl. Acad. Sci. U.S.A.* 92, 1769-1773; Görlich, D., et al. (1995) *Curr. Biol.* 5, 383-392; Chi, N. C., et al. (1995) *J. Cell Biol.* 130, 265-274. Kap β1 interacts with nuclear pore complex (NPC) proteins and appears to mediate movement of the import complex through the NPC via these interactions. Rexach, M., and Blobel, G. (1995) *Cell* 83, 683-692; Radu, A., Blobel, G., and Moore, M. S. (1995) *Proc. Natl. Acad. Sci. U.S.A.* 92, 1769-1773; Iovine, M. K., Watkins, J. L., and Wente, S. R. (1995) *J. Cell Biol.* 131, 1699-1713; Radu, A., Moore, M. S., and Blobel, G. (1995) *Cell* 81, 215-222. Another protein, p10/NTF2, has also been implicated in nuclear import, but its function may only be to take Ran into the nucleus, where it is subsequently needed to disassemble an incoming import complex. Moore, M. S., and Blobel, G. (1994) *Proc. Natl. Acad. Sci. U.S.A.* 91, 10212-10216; Paschal, B. M., and Gerace, L. (1995) *J. Cell Biol.* 129, 925-937; Ribbeck, K., Lipowsky, G., Kent, H. M., Stewart, M., and Görlich, D. (1998) *EMBO J.* 17, 6587-6598; Smith, A., Brownawell, A., and Macara, I. G. (1998) *Curr. Biol.* 8, 1403-1406.

Although there is only one Kap α homologue in yeast (SRP1 or Kap60), vertebrate cells contain a number of proteins that can bind a classical NLS and share sequence homology (see Ref. Nachury, M. V., Ryder, U. W., Lamond, A. I., and Weis, K. (1998) *Proc. Natl. Acad. Sci. U.S.A.* 95, 582-587, and references therein). These proteins have been given a variety of names but can be grouped into three major families. The Kap α1 family contains the human protein NPI-1/importin α1/karyopherin α1/Rch2/hSRP1 and a second related protein importin α6, in addition to the mouse S2 protein. Moroianu, J., et al., (1995) *Proc. Natl. Acad. Sci. U.S.A.* 92, 2008-2011; Cortes, P., et al. (1994) *Proc. Natl. Acad. Sci. U.S.A.* 91, 7633-7637; O'Neill, R. E., et al., (1995) *J. Biol. Chem.* 270, 22701-22704; Kohler, M., et al., (1997) *FEBS Lett.* 417, 104-108; Tsuji, L., et al., (1997) *FEBS Lett.* 416, 30-34. The second family, Kap α2, contains human Rch1/hSRP1/importin α2/karyopherin α2 and the mouse protein pendulin/PTAC 58. Görlich, D., Prehn, S., Laskey, R. A., and Hartmann, E. (1994) *Cell* 79, 767-778; Cuomo, C. A., Kirch, S. A., Gyuris, J., Brent, R., and Oettinger, M. A. (1994)

*Proc. Natl. Acad. Sci. U.S.A.* 91, 6156-6160; Kussel, P., and Frasch, M. (1995) *Mol. Gen. Genet.* 248, 351-363; Imamoto, N., Shimamoto, T., Takao, T., Tachibana, T., Kose, S., Matsubae, M., Sekimoto, T., Shimonishi, Y., and Yoneda, Y. (1995) *EMBO J.* 14, 3617-3626; K., Mattaj, I. W., and Lamond, A. I. (1995) *Science* 268, 1049-53. The third family, Kapα3, consists of the two human proteins, QIP-1/importin α3 and KPNA3/hSPR1 γ/hSRP4, and the mouse proteins Q1 and Q2. Nachury, M. V., et al., (1998) *Proc. Natl. Acad. Sci. U.S.A.* 95, 582-587; Kohler, M., et al., (1997) *FEBS Lett.* 417, 104-108; Tsuji, L., et al., (1997) *FEBS Lett.* 416, 30-34; Takeda, S., et al., (1997) *Cytogenet. Cell Genet.* 76, 87-93; Seki, T., et al., (1997) *Biochem. Biophys. Res. Commun.* 234, 48-53; Miyarnoto, Y., et al., (1997) *J. Biol. Chem.* 272, 26375-26381. Each of these classes share about 50% homology with each other and to the yeast SRP1, and each of these mammalian proteins has been shown to be capable of mediating the import of one or more classical NLS-containing proteins. Nachury, M. V., et al., (1998) *Proc. Natl. Acad. Sci. U.S.A.* 95, 582-587; Sekimoto, T., et al., (1997) *EMBO J.* 16, 7067-7077; Nadler, S. G., et al., (1997) *J. Biol. Chem.* 272, 4310-4315; Prieve, M. G., et al., (1998) *Mol. Cell. Biol.* 18, 4819-4832.

Stat-1 import is mediated by Kapα1/NPI-1 but not Kapα2/Rch1, but activated Stat-1 appears to bind to a COOH-terminal region of Kapα1 distinct from the NLS binding Armadillo repeats. The binding differences of the different Kapαs to RCC1 observed appear to be due solely to the NLS on RCC1 and therefore probably due to the NLS binding region of Kapα3. Sekimoto, T., et al., (1997) *EMBO J.* 16, 7067-7077. Kamei, Y., et al., (1999) *J. Histochem. Cytochem.* 47, 363-372 showed that, in mice, the Kapα3 homologue is expressed in many tissues and theorized that Kapα3 may play a role in importing "a limited number of unique karyophilic proteins, such as helicase Q1." The results provided by Talcott, B. and Moore, M. S., 2000 *J Biol Chem*, 275(14) 10099-10104 suggest that RCC1 should be included in the group of proteins that use Kapα3 to mediate their nuclear import.

U.S. Pat. No. 6,191,269 teaches the existence of a nuclear localization sequence contained within the cDNA sequence of the N-terminal IL-1 alpha propiece, T76-NGKVLKKRRL (SEQ ID NO:1), which had characteristics of a nuclear localization sequence (NLS) and could mediate nuclear localization of the propiece (Stevenson et al. (1997) *Proc. Natl. Acad. Sri. USA* 94:508-13. Introduction of the cDNA encoding the N-terminal IL-alpha propiece into cultured mesangial cells resulted in nuclear accumulation (Stevenson et al. id).

U.S. Pat. No. 5,877,282 teaches that the antennapedia homeodomain signal sequence peptide is the amino acid sequence RQIKLWFQNRRMKWKK (SEQ ID NO:2); the fibroblast growth factor signal sequence peptide is AAVALLPAVLLALLA (SEQ ID NO:3); the HIV Tat signal sequence peptide is the amino acid sequence CFITKALGISYGRKKRRQRRRPPQGSQTH (SEQ ID NO:4).

Schwartze, S. R., et al., *Science* 285:1569-1572 (1999) report delivery of an ip injected reporter protein, 116 kD beta-galactosidase, as a TAT fusion protein into tissues and across the blood-brain barrier. Schwartze used an 11 amino acid protein transduction domain (PTD) derived from HIV tat protein with an N-terminal fluorescein isothiocyanate (FITC)-Gly-Gly-Gly-Gly (SEQ ID NO:5) motif. The authors report that earlier attempts to transduce beta-Gal chemically cross-linked to the TAT PTD resulted in sporadic and weak beta-Gal activity in a limited number of tissues. They speculate that the improved transduction was due to the in-frame fusion and purification strategy used.

Nuclear localization of IFNγ is mediated by a polybasic NLS in its C terminus, which is required for the full expression of biological activity of IFNγ, both extracellularly and intracellularly. Subramaniam, Prem S., et al., *J. Cell Sci.* (2000), 113(15), 2771-2781. This NLS is thought to play an integral intracellular role in the nuclear translocation of the transcription factor STAT1α activated by IFNγ because treatment of IFNγ with antibodies to the C-terminal region (95-133) containing the NLS blocked the induction of STAT1α nuclear translocation, but these antibodies had no effect on nuclear translocation of STAT1α in IFNα treated cells. A deletion mutant of human IFNγ, IFNγ(1-123), which is devoid of the C-terminal NLS region was biologically inactive, but was still able to bind to the IFNγ receptor complex on cells with a $K_d$ similar to that of the wild-type protein. Deletion of the NLS specifically abolished the ability of IFNγ(1-123) to initiate the nuclear translocation of STAT1α, which is required for the biological activities of IFNγ following binding to the IFNγ receptor complex. A C-terminal peptide of murine IFNγ, IFNγ(95-133), that contains the NLS motif, induced nuclear translocation of STAT1α when taken up intracellularly by a murine macrophage cell line. Deletion of the NLS motif specifically abrogated the ability of this intracellular peptide to cause STAT1α nuclear translocation. In cells activated with IFNγ, IFNγ was found to as part of a complex that contained STAT1α and the importin-α analog Npi-1, which mediates STAT1α nuclear import. The tyrosine phosphorylation of STAT1α, the formation of the complex IFNγ/Npi-1/STAT1α complex and the subsequent nuclear translocation of STAT1α were all dependent on the presence of the IFNγ NLS.

The peptide representing amino acids 95-132 of IFN (IFN-γ (95-132)), containing the polybasic sequence $^{126}$RKRKRSR$^{132}$ (SEQ ID NO:6), was capable of specifying nuclear uptake of the autofluorescent protein, APC, in an energy-dependent fashion that required both ATP and GTP. Nuclear import was abolished when the above polybasic sequence was deleted. Subramaniam, P., et al., 1999 *J Biol Chem* 274(1) 403-407. A peptide containing the prototypical polybasic NLS sequence of the SV40 large T-antigen was also able to inhibit the nuclear import mediated by IFN-γ (95-132), suggesting that the NLS in IFN may function through the components of the Ran/importin pathway utilized by the SV40 T-NLS. Intact IFN-γ, when coupled to APC, was a iso able to mediate its nuclear import, and this nuclear import was blocked by the peptide IFN-γ (95-132) and the SV40 T-NLS peptide, suggesting that intact IFN-γ was also transported into the nucleus through the Ran/importin pathway.

Nuclear proteins are imported into the nucleus through aqueous channels that span the nuclear envelope called nuclear pore complexes (NPCs). Although ions and molecules less than ~20-40 Da can diffuse passively through the nuclear pore complexes, larger proteins are transported by saturable pathways that are energy- and signal-dependent. The signals that specify nuclear protein import (NLSs) are commonly short stretches of amino acids rich in basic amino acid residues, although other classes of NLSs have been described recently. The initial step in the import of proteins containing basic amino acid-type NLSs occurs in the cytosol, where the NLS-containing proteins are bound to a receptor (variously called the NLS receptor, importin α, and karyopherin (13). The substrate-receptor complex then associates with the cytoplasmic face of the nuclear pore complexes, and with the participation of other cytosolic factors, is transported through a gated channel in the nuclear pore complexes to the nuclear interior. The in vivo events of NLS-mediated nuclear import can be duplicated in an in vitro system using digitonin-permeabilized cells supplemented with cytosolic extracts and ATE (14). Transport in this in vitro assay is blocked by the same inhibitors that block in vivo import, is rapid, and is easily quantified.

The NLS the sequence NYKKPKL (SEQ ID NO:7) in the N-terminus of fibroblast growth factor (FGF)-1, the precursor for acidic FGF, has been proposed to affect the long term activities of FGF-1 through its function as a nuclear translocation signal or its role in stabilization of the structure required to sustain binding and activation of the transmembrane receptor kinase. Luo, Y., et al., *J. Biol. Chem.* (1996), 271(43). 26876-26883. For example, concurrent with a marked increase in dependence on exogenous heparin for optimal activity, sequential deletion of residues in the NYKKPKL (SEQ ID NO:7) sequence in FGF-1 resulted in a progressive loss of thermal stability, resistance to protease, mitogenic activity, and affinity for the transmembrane receptor. The largest change resulted from deletion of the entire sequence through the lysine-leucine residues. In the presence of sufficiently high concentrations or heparin, the deletion mutants exhibited mitogenic activity equal to wild-type FGF-1.

Although FGF-1 contains a nuclear translocation sequence (NTS), nuclear translocation requires an exogenous and not an endogenous pathway. The NTS of FGF-1 NYKKPKL (SEQ ID NO:7), is able to direct the expression of the bacterial β-galactosidase (βgal) gene to the nucleus of transfected NIH 3T3 cells, but this NTS is unable to target either FGF-1 itself of a FGF-1-βgal fusion protein into tire nucleus, suggesting that FGF-1 may contain an additional sequence which prevents endogenously expressed FGF-1 from being translocated into the nucleus. Zhan, X., et al., *Biochem. Biophys. Res. Commun.* (1992), 188(3), 982-91.

Interferon-γ (IFN-γ), a protein that uses the Jak-Stat pathway for signal transduction, translocates rapidly to the nucleus in cells treated extracellularly with the cytokine. An NLS has been identified and characterized in the C-terminus of human and murine IFN-γ. Larkin, J., et al., *J. Interferon Cyokine Res.* (2001), 21(6), 341-348 report that human IFN-γ (HuIFN-γ) contains a second NLS at an upstream site. The primary sequence, analogous with the NLS sequence identified in murine IFN-γ, representing amino acids 122-132 of HuIFN-γ was capable of mediating the nuclear import of the autofluorescent protein allophycocyanin (APC) in an energy-dependent manner. The second sequence, representing amino acids 78-92 of HuIFN-γ, was also capable of mediating the nuclear import of APC in an energy-dependent manner but to a greatly reduced extent. The nuclear import of both sequences conjugated to APC was strongly blocked by competition with unconjugated HuIFN-γ(122-132). Competition by the sequence HuIFN-γ(78-92) effectively blocked the import of APC-conjugated HuIFN-γ(78-92) but, at the same concentration, was not capable of inhibiting the nuclear import of APC-conjugated HuIFN-γ(122-132), suggesting that HuIFN-γ(78-92) was a less efficient NLS than HuIFN-γ (122-132). This is consistent with >90% loss of antiviral activity of HuIFN-γ lacking the downstream NLS in 122-132. The nuclear import of APC-conjugated HuIFN-γ(122-132) was inhibited by a peptide containing the prototypical polybasic NLS of the SV40 T NLS, which suggests that the same Ran/importin cellular machinery is used in both cases.

There appears to be strong conservation of the NLS motif as a mechanism for nuclear localization. Evolution seemed to have used part of the existing DNA-binding mechanism when compartmentalizing DNA-binding proteins into the nucleus. Cokol, M., et al., *EMBO Rep.* (2000), 1(5), 411-415 estimate that greater than 17% of all eukaryotic proteins may be imported into the nucleus, and after analyzing a set of 91 experimentally verified NLSs from the literature and expanding this set to 214 potential NLSs through iterated "in silico mutagenesis". This final set matched in 43% of all known nuclear proteins and in no known non-nuclear protein. Cokel et al found an overlap between the NLS and DNA-binding region for 90% of the proteins for which both the NLS and DNA-binding regions were known, but only 56 of the 214 NLS motifs overlapped with DNA-binding regions. These 56 NLSs enabled a de novo prediction of partial DNA-binding regions for approximately 800 proteins in human, fly, worm and yeast.

More recently, it has been reported that NLS signal peptide can induce structural changes of DNA. The plant enzyme, glutaminyl-tRNA synthetase (GlnRS) from Lupinus luteus, contains an NLS at the N-terminal, a lysine rich polypeptide, KPKKKKEK (SEQ ID NO:8) Krzyzaniak, A., et al. *Mol. Biol. Rep.* (2000), 27(1), 51-54. Two synthetic peptides (20 and 8 amino acids long), derived from the NLS sequence of lupin GlnRS interact with DNA. In addition, the shorter 8 amino acid peptide caused the DNA to change its conformation from the B to the Z form. This observation clearly suggests that the presence of the NLS polypeptide in a leader sequence of GlnRS is required not only for protein transport into nucleus but also for regulation of a gene expression. This is the first report suggesting a role of the NLS signal peptide in structural changes of DNA.

Typically there is strong conservation of the NLS sequence within species. For example, the NLS in the N-terminal region of Smad 3 protein, the major Smad protein involved in TGF-β signal transduction, has a basic motif $Lys^{40}$-Lys-Leu-Lys-$Lys^{44}$ (SEQ ID NO:9), which is conserved among all the pathway-specific Smad proteins, and is required for Smad 3 nuclear import in response to ligand. Smad proteins are intracellular mediators of transforming growth factor-β (TGF-β) and related cytokines. Xiao, Z., et al., *J. Biol. Chem.* (2000), 275(31), 23425-23428 identified the role the NLS plays in nuclear localization. The authors demonstrated that the isolated Smad 3 MH1 domain displays significant specific binding to import in β, which is diminished or eliminated by mutations in the NLS. Full-size Smad 3 exhibits weak but specific binding to importin β, which is enhanced after phosphorylation by the type 1 TGF-β receptor. In contrast, no interaction was observed between importin α and Smad 3 or its MH1 domain, indicating that nuclear translocation of Smad proteins may occur through direct binding to importin β. The authors conclude that activation of all of the pathway-specific Smad proteins (Smads 1, 2, 3, 5, 8, and 9) exposes the conserved NLS motif, which then binds directly to importin β triggers nuclear translocation.

In all cells, the lipid bilayer of cell membranes serves as a selective barrier for the passage of charged molecules, with the internalization of hydrophilic macromolecules being achieved through classical transport pathways (Hawiger, J., *Curr Opin Chem Biol.* 3, 89-94 (1999), Schwarze, S. R., et al., *Trends in Cell Biology* 10, 290-295 (2000)). These classical mechanisms of internalization involve receptor-mediated endocytosis or transporter dependent uptake (Cleves, A. E., *Current Biology* 7, R318-R320 (1997)). In contrast, an increasing number of molecules have been discovered that lack classical import and/or export signals (Cleves, A. E., *Current Biology* 7, R318-R320 (1997)). These molecules gain direct access to either cytoplasmic or nuclear compartments using unconventional processes of which the mechanisms remain largely unknown. These novel mechanisms are generally termed "nonclassical" and refer to transport pathways being used that are atypical. Relevant examples of this latter type are found in the gene-encoded proteins of HIV-1

TAT (Frankel, A. D. and Pabo, C. O. *Cell* 55, 1189-1193 (1988)), herpes virus VP22 (Elliott, C. and O'Hare, P. *Cell* 88, 223-233 (1997)), and Antennapedia, Antp (Derossi, D., et al., *J. Biol. Chem.* 269, 10444-10450 (1994)). It is now well established that the full-length proteins of HIV-1 TAT (Helland D. E., et al., *J Virol* 65, 4547-4549 (1991)), and VP22 (Pomeranz L. E. and Blaho J. A., *J Virol* 73, 6769-6731 (1999)) rapidly translocate into and out of cellular membranes. In fact, distinct peptide regions have been identified within both of these proteins that are capable of translocating into cellular compartments either alone or in combination with chimeric cargo peptides, and proteins (Lindgren, M, et al., *Trends Pharmacol Sci.* 3, 99-103 (2000), Derossi, D., et al, *Trends Cell Biol.,* 8, 84-87 (1998), Prochiantz A., *Current Opinion in Cell Biology* 12, 400-406 (2000), Steven R. Schwarze, S. R., et al., *Trends in Cell Biology* 10, 290-295 (2000)). In contrast, full-length Antp protein has not been shown to traverse biological membranes; however, a 16 amino acid synthetic peptide derived from within its coding region does possess potent membrane penetrating abilities (Derossi, D., et al, *Trends Cell Biol.,* 8, 84-87 (1998)). The accepted view of atypical transport used by these molecules has been termed "transduction" (Schwarze, S. R., et al. *Trends in Cell Biology* 10, 290-295 (2000)), and is currently defined as an extremely rapid membrane transport pathway that is receptor and energy independent, and can occur at 4° C. in all cell types (Schwarze, S. R. and Dowdy, S. F. *Trends Pharmacol. Sci.* 21, 45-48 (2000)). Interestingly, these three proteins are all nuclear proteins involved in transcriptional regulation, and their respective transducing peptides consist of strings of amino acids rich in arginine and lysine (Lindgren, M., et al., *Trends Pharmacol Sci.* 3, 99-103 (2000). Schwarze, S. R. and Dowdy, S. F. *Trends Pharmacol. Sci.* 21, 45-48 (2000)). However, irrespective of these similarities, these transducing peptides possess many different characteristics such as amino acid sequence, length of the sequence, cellular localization, and potency of membrane penetration. Thus, though each transducing sequence can penetrate cells and tissues, it has not been established whether they use the identical atypical transport mechanisms.

Finally, U.S. Pat. No. 6,022,950 teaches the use of a hybrid molecule of a portion of the binding domain of a cell-binding polypeptide ligand effective to cause said hybrid protein to bind to a cell of an animal, a translocation domain of naturally occurring protein which translocates said third part across the cytoplasmic membrane into the cytosol of the cell; and a chemical entity to be introduced into the cell. However, the patent teaches translocation domains of toxins. Naturally-occurring proteins which are known to have a translocation domain include diphtheria toxin and *Pseudomonas* exotoxin A, and may include other toxins and non-toxin molecules, as well. The translocation domains of diphtheria toxin and *Pseudomonas* exotoxin A are well characterized (see, e.g., Hoch et al., Proc. Natl. Acad. Sci. USA 82:1692-1696, 1985; Colombatti et al., J. Biol. Chem. 261:3030-3035, 1986; and Deleers et al., FEBS 160:82-86, 1983), and the existence and location of such a domain in other molecules may be determined by methods such as those employed by Hwang et al., Cell 48:129-136, 1987; and Gray et al., Proc. Natl. Acad. Sci. USA 81:2645-2649, 1984.

Given the considerable body of literature teaching control mechanisms of cellular localization, the proteins involved in regulation of intracellular transport, the different properties and control mechanisms for plasma membrane and the nuclear envelope, it is unexpected that polypeptides derived from mammalian proteins could transduce through the plasma membrane using nonclassical mechanisms and thus could be useful as membrane penetrating peptides useful as in vitro, ex vivo and in vivo delivery devices of a compound of interest. There is also considerable literature teaching nonprotein derived methods for delivering a compound of interest into cells, for example electroporation, membrane fusion with liposomes, high velocity bombardment with DNA-coated microprojectiles, incubation with calcium-phosphate-DNA precipitate, DEAE-dextran mediated transfection, infection with modified viral nucleic acids, and direct microinjection into single cells, usually ova and the like. Each of these methods is relatively inefficient, resulting in relatively low percentage of the cells containing the delivered compound of interest and most of the methods are clearly not capable of realistic in vivo delivery. Many of the methods are toxic to the cells, resulting in relatively high apoptosis. Therefore, there is a considerable need for simple and more efficient delivery of compounds of interest into cells.

SUMMARY OF THE INVENTION

The present invention is directed to polypeptides derived from mammalian and yeast proteins useful as a carrier for in vitro, ex vivo and in vivo delivery a compound of interest. The invention also provides compositions containing the same, and methods of delivering a compound of interest in vitro, ex vivo and in vivo.

BRIEF DESCRIPTION OF THE DRAWINGS

Figure 1A:
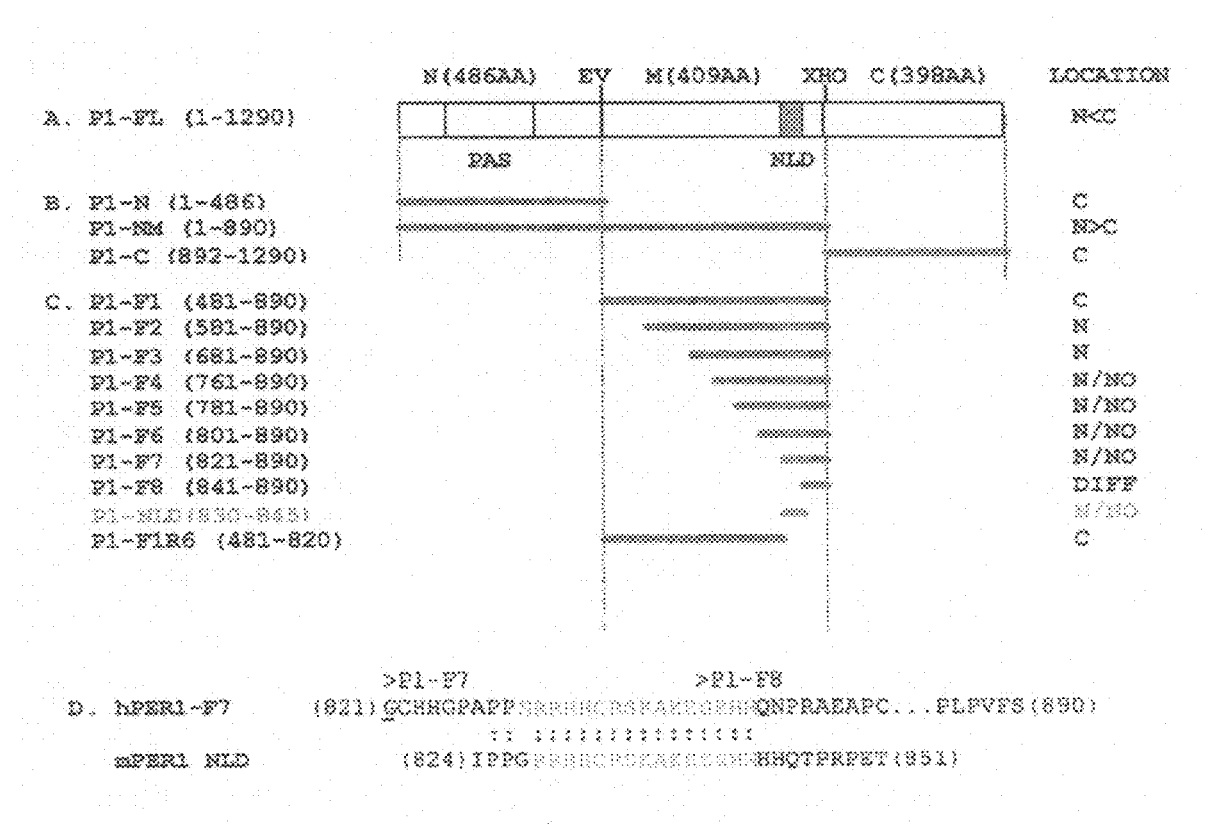

FIG. 1. (B). Cellular localization of hPER1 fusion proteins as described in FIG. 1A, above, in living cells. CHO cells were transient transfected with the fusion constructs indicated on the top of each panel and the subcellular localization of EYFP reporters was directly visualized using fluorescent microscopy 10 h post-transfection. EYFP vector alone is used as control (see 5.EYFP-VECTOR)

FIG. 4 (B). Dose response of PTM7 (closed circles) and TTM7 (closed diamonds) peptides. Serotonin (control, open triangle) was used at the maximum receptor stimulatory concentration of 10 μM.

DETAILED DESCRIPTION OF THE INVENTION

Figure 1B:
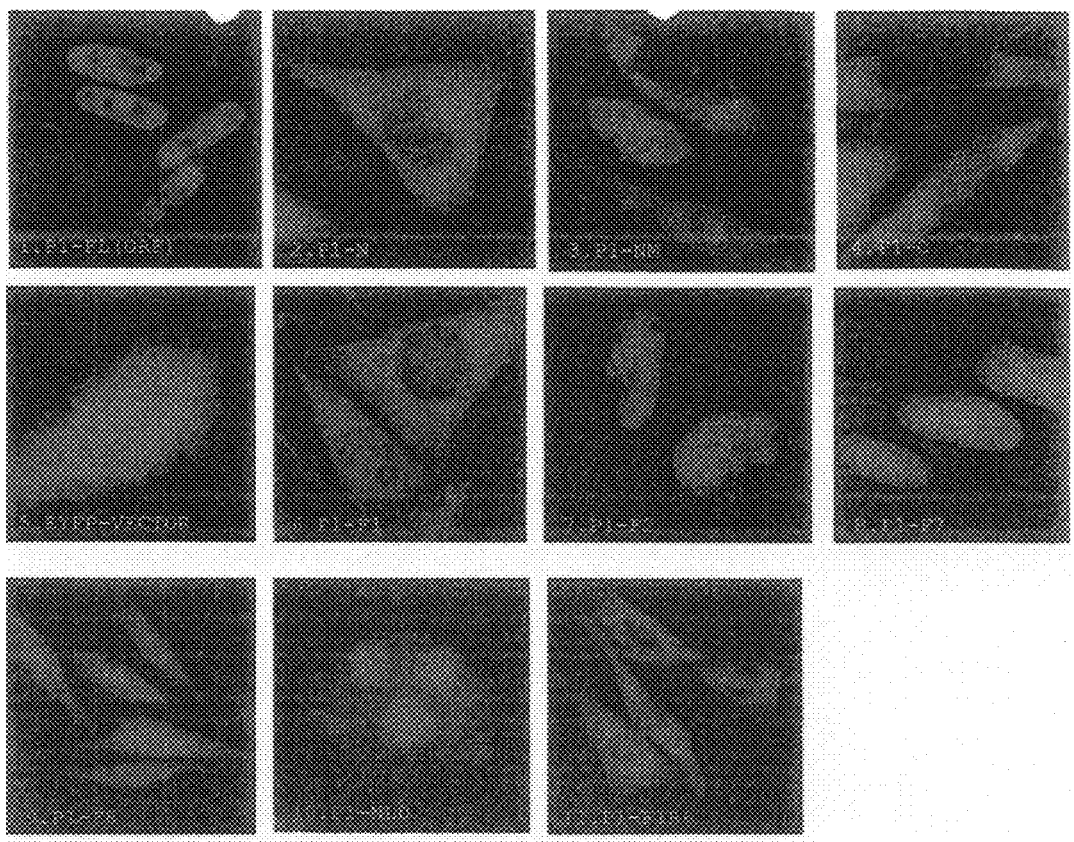
FIG. 1. (A). Schematic diagram of hPER1 fusion constructs showing the locations of the PAS, cytoplasmic localization, and nuclear localization sequence (NLS, but indicated as nuclear localization domain (NLD) in Figure). The name and the position of the fusion constructs are listed on the left. The number indicates the first and last amino acid residues in the hPER1 protein. The principal sites of accumulation of each fusion protein are summarized on the right, (n) nuclear, (no) nucleoli, (c) cytoplasmic, (diff) diffuse. All constructs were N-terminally tagged with EYFP. The alignment human and mouse PER1-NLS is shown at the bottom.

The present invention is based on discovery that human Period 1 (hPER1) protein contains an NLS which has now also been identified as an MPP and is useful as a delivery device for intracellular delivery of a compound of interest. hPER1 is involved in regulation of the circadian rhythm and the capacity of hPER1 to translocate to adjacent cells may be critical to its overall biological function of regulating circadian rhythm. The NLS identified within hPER1 does not fit within previously identified NLS sequences, and its identification has resulted in identification of an algorithm for searching for other NLS sequences which may also function as MPPs.

Period 1 (hPER1) is a nuclear protein involved with transcriptional regulation. It is an essential component in the "gears" of the biological clock (Brown, S. A., and Schibler, U., Current Opinion in Genetics & Development 9, 588-594 (1999), Dunlap, J. C., Cell 96, 271-290 (1999)), and studies in mice have shown that nuclear entry of PER1 is essential for the down regulation of CLOCK/BMAL transcriptional complexes (Gekakis N, et al., Science 280, 1564-1569. (1998), Yagita, K., et al., Genes Dev 14, 1353-1363 (2000), Lowrey, P. L., et al., Science 288, 483-492 (2000)). However, to date, the functional NLS for human PER1 has not been elucidated. The present inventors identified the NLS within hPER1, and demonstrate that the 16 amino acid and 13 amino acid sequence, see FIG. 3. hPER1-NLS peptide, hPER1-MPP, has potent membrane penetrating ability. This work results in the identification of four additional MPPs also derived from nuclear proteins.

PER1 is a central component in the circadian clock, and its nuclear entry plays an important role in the regulation of daily oscillations (Jin, X., et al., Cell 96, 57-68 (1999), Sangoram, A. M., et al., Neuron 21, 1101-13 (1998)). Using deletion and fusion protein analysis, we identified a NLS that is necessary and sufficient for hPER1 nuclear localization. This functional analysis was necessary because the NLS of hPER1 does not conform to classical nuclear localizing consensus motifs; and therefore, was not identified using standard NLS search procedures. We show that a single copy of hPER1-NLS is sufficient for inducing nuclear localization of a reporter protein and of tagged hPER1 fragments (P1-F2 to P1-F7) in transfected cells. The PER1-NLS is located between amino acids (830-845) of hPER1, is embedded within a string of 13 amino acids rich in arginine, histidine, and lysine (see Table 1) that is not found in other PERs or other nuclear proteins in available databases. Therefore, though PERs 2 and 3 are nuclear proteins (Jin, X., et al., Cell 96, 57-68 (1999)), they apparently use alternative sequences and or mechanisms for their nuclear import.

Peptide fragments of a limited number of nuclear proteins that are rich in basic residues have been shown to penetrate into cellular membranes in a receptorless, energy-independent fashion. Sequences from three such proteins, TAT, Antp, and VP22 have been demonstrated to possess the ability to penetrate and cargo fusion molecules into cells and tissues by an as yet undefined mechanism. See, for example, U.S. Pat. Nos. 5,804,604, 5,747,641, 5,674,980, 5,670,617 and 5,652,122 issued to Frankel et al., which teach the use of a nine-amino acid HIV TAT-derived polypeptide (Arg-Lys-Lys-Arg-Arg-Gln-Arg-Arg-Arg (SEQ ID NO:12)) for intracellular delivery of cargo molecules.

The similarities between hPER1, the hPER1-NLS, and other MPPs prompted us to investigate whether or not hPER1-MPP could have membrane penetrating capability. The immunohistochemical and cytological data presented herein indicates that the hPER1-MPP functions as a MPP in a variety of cell types. hPER1-MPP demonstrated intense focal staining in the nuclear plasma as well as in the nucleolus, suggesting that the subnuclear address of hPER1-MPP is different from the hPER1 (P1-FL) protein that was diffused in the nucleus but not concentrated in the nucleolus. The cellular penetration of hPER1-MPPs is not blocked even under the conditions of reversing the sequence (reversed hPER1-MPP), adding negatively charged residues or pre-fixing cells with 4% PFA, unpublished observation, the latter supports the idea that penetration is receptor and membrane independent. These results are in contrast to other peptide classes that have been described that are derived from signal peptide sequences (Hawiger, J., *Curr Opin Immunol.* 9, 189-94 (1997)), DNA antibodies (Deng, S. X., et al., *Int Immunol.* 12, 415-423 (2000)), and other protein domains (Lindgren, M., et al., *Trends Pharmacol Sci.* 3, 99-103 (2000)) that bind and cross the cell membranes using slow, temperature, energy, and receptor dependent mechanisms.

The identification of other MPPs, has been limited by our lack of understanding the mechanisms and structural requirements necessary for membrane peptide penetration. The likelihood that a specific peptide structure and/or charge is important for membrane penetration is demonstrated in the alanine scanning experiments whereby a single amino acid change at arginine 7 appears to be critical for MPP potential. By comparing wild-type hPER-MPP to modified P1-R7A, in live cells or pre-fixed and permeabilized cells (data not show), P1-R7A is only defective in penetration but not in nuclear targeting once the cells have been permeabilized. This finding suggests that arginine 7 has a major role in structure based penetration, and thus provides a useful model for the future structure-function studies. No structural determinants for TAT peptide have been described, but in the case of Antp, replacing the two tryptophan residues with two phenylalanines abolishes penetration (Le Roux, I., et al., *Proc Natl Acad Sci USA.* 90, 9120-9124 (1993)). Since hPER1-MPP does not contain any tryptophan residues, membrane penetration between these two peptides may occur by different mechanisms.

Full-length HIV TAT and VP22, both of which lack classical secretary signal sequences and are therefore exported by non-classical mechanisms, can also be imported "by transduction", into cells in a non-classical manner (Prochiantz A., *Current Opinion in Cell Biology* 12, 400-406 (2000)). Therefore, it is interesting to speculate that perhaps hPER1 distributes circadian clock information to adjacent SCN neurons or to circadian output pathways by "transduction" mechanisms similar to full-length TAT and VP22 proteins. However, simply having membrane penetrating sequences within the body of a protein does not necessarily confer membrane penetrating capability, as full-length Antp protein is neither exported from nor imported into cells. Thus, the non-classical penetration of the Antp peptides into the cells is unlikely to have physiological relevance, and like Antp, there is no evidence to suggest that full-length hPER1 is a cell membrane penetrating protein. However, these findings did encourage us to search for other MPP-containing proteins. By searching protein databases with an algorithm designed to identify strings of basic residues within nuclear proteins, we uncovered hundreds of proteins that contained potential membrane penetrating peptide regions and found 4 additional MPPs from several species (see FIG. 5). These and additional database mining searches suggest that MPP-like sequences are common, and present within a wide variety of proteins. However, like many putative NLSs that do not always confer nuclear localization when fused to reporter sequences (Moroianu, J., *J Cell Biochem.* 32-33, 76-83 (1999)), any potential MPPs must be functionally determined experimentally. Though it seems clear that either transducing or non-transducing proteins can encode MPP regions, the interesting question that remains is whether or not proteins containing MPP-like sequences use these domains to rapidly translocate intracellularly into cellular domains to activate normal physiological processes. The efficiency associated with the transduction phenomena might be particularly useful where the rapid delivery of intercellular information is critical, as may be the case in cell synchronization, development, and differentiation paradigms.

The ability for MPPs to cargo molecules to intracellular compartments is becoming well-established (Lindgren, M., et al., *Trends Pharmacol Sci.* 3, 99-103 (2000), Derossi, D., et al, *Trends Cell Biol.,* 8, 84-87 (1998)). Similar to other MPPs, hPER1-MPP and other MPPs identified herein can deliver compounds of interest, such as large molecules, i.e., peptides and proteins, lipids, polysaccharides, other organic molecules, rapidly and efficiently into cells. The data presented herein demonstrates that hPER1-MPP in fusion with either serotonergic and/or adrenergic 7TM-receptor derived peptides mimic the effects of ligand activated receptors (see FIG. 4, and data not shown), confirming that hPER1-MPP translocates compounds of interest to intracellular compartments, and supports the idea that physiologically relevant signaling can be initiated by MPPs linked to compounds of interest. Using the methods described herein, the present invention may be expanded to provide target validation using MPPs linked to targets, and/or therapeutic strategies using MPPs linked to specific enzymes or receptors as a method of altering, correcting or compensating for dysfunctional enzyme performance or within pathways. In addition, therapeutic strategies using MPPs linked to specific receptors may be used as a method of altering, correcting or compensating for dysfunctional receptor, low expression of normal or abnormal receptors.

Taken together, the results provided herein demonstrate an MPP encoded by a mammalian protein and more specifically, a human nuclear protein, whose cellular penetration is membrane independent and likely depends on the peptide structure. hPER1-MPP targets to specific subnuclear sites, but has the potential to efficiently deliver other macromolecules to intracellular targets.

More importantly, this invention also provides the first example for mapping a novel MPP based on a NLS domain, and suggests that many MPP-like regions are contained within a wide variety of proteins. The data provided herein demonstrate that an MPP may be based on part of an NLS, or overlap with part of the NLS, or alternatively, may be a novel peptide.

Methods of identifying NLS sequences are well known in the art, and include NLSs previously identified as conferring the ability of the native protein to enter the nucleus, or is a putative NLS based on substantial sequence homology with a previously identified NLS. Alternatively, the NLS may be identified by sequence deletion experiments. See for example, Luo J C, Shibuya M A variant of nuclear localization signal of bipartite-type is required for the nuclear translocation of hypoxia inducible factors (1alpha, 2alpha and 3alpha). Oncogene. 2001 Mar. 22; 20(12):1435-44 or Hodel M R Corbett A H Hodel A E. Dissection of a nuclear localization signal. J Biol Chem. 2001 Jan. 12; 276(2):1317-25.

Preferred membrane penetrating peptides (MPPs, also known as peptide transduction domain or 'PTD') of the present invention are small polypeptides, and may be derived from an NLS, or overlapping with an NLS, of a mammalian or yeast protein. Preferred mammalian proteins are those of human, primate, marine or rat species. It is generally preferred to use the same species for the NLS-derived protein as the cell to be treated. Human species are especially preferred as the NLS-derived protein when being used to treat human cells. NLSs may be found within a broad class of enzymes, and is not limited to nuclear proteins, transcription factors, cytokines and kinases. Preferred MPPs are those derived from nuclear proteins or transcription factors. Alternatively, MPPs of the present invention are small polypeptides comprising a sequence-(X-X-X-X)$_n$-(SEQ ID NO:54) where n is an integer 1 to 7, and X each time is independently selected from the group consisting of arginine, histidine or lysine. It is preferred that small MPPs are used, and therefore, it is preferred that n is an integer 1 to 5, and more preferred that n is an integer 1 to 3. Selected embodiments of suitable MPPs are provided in Table 1 and Example 5.

The MPP and/or compound of interest may be chemically synthesized separately, for example, by chemical synthetic routes and using commercially available reagents. Alternatively, if the MPP and/or compound of interest is a polypeptide, it may be synthesized by recombinant technology and purified according to known methods. Host cells, cloning vectors, promoters and oligonucleotide linkers are well known and commercially available. Methodologies for using recombinant technology and purification methods are also well known, see Current Protocols in Molecular Biology, 4 Vols. Wiley. Generally, recombinant technology is preferred, as it is more amenable to larger scale production and is more economical for mass production. Alternatively, MMPs may be obtained by specific protease degradation of a precursor proteins.

The compound of interest may be attached or linked to the MPP via chemical crosslinking at the N- or C-terminus of the MPP to create a conjugated (also referred to a fusion) MPP and compound of interest, for example, via disulfide or ester linkages. In an alternative embodiment, if the compound of interest is a peptide, the peptide may be synthesized by recombinant technology with a host cell with an expression vector encoding a fusion of the MPP sequence and the compound of interest under conditions to permit expression of the vector and obtaining the fusion MPP and compound of interest.

In another embodiment, the MPP and the compound of interest may be attached or linked via a chemical linker. Chemical linkers are well known in the art, and include but are nor limited to dicyclohexyl carbodiimide (DCC), N-hydroxysuccinimide (NHS), maleiimidobenzoyl-N-hydroxysuccinimide ester (MBS), N-ethyloxycarbonyl-2-ethyloxy-1,2-dihydroquinoline (EEDQ), N-isobutyloxy-carbonyl-2-isobutyloxy-1,2-dihydroquinoline (IIDQ). Preferred linkers may also be monomeric entities such as a single amino acid, especially preferred are those amino acids with small side chains, or a small polypeptide chain, or polymeric entities of several amino acids. Preferred polypeptide linkers are fifteen amino acids or less, more preferred are polypeptide linkers of ten or less amino acids. Even more preferred are polypeptide linkers of five or less amino acids in an alternative embodiment, the linker may be a nucleic acid encoding a small polypeptide chain; preferred linkers encode a polypeptide of fifteen or less amino acids. More preferred linkers are nucleic acids encoding a small polypeptide chains of ten or less amino acids. Even more preferred linkers are nucleic acid encoding a small polypeptide of five or less amino acids, such as Gly-Phe-Leu-Gly (SEQ ID NO:13), Gly-Gly, Gly-Leu or Gly, and the like.

Recombinant technology may be used to express a fusion MPP, linker and compound of interest, as described above and is well known in the art.

In another embodiment, the linker may be a cleavable linker, resulting in cleavage of the MPP and compound of interest once delivered to the tissue or cell of choice. In such an embodiment, the cell or tissue would have endogenous (either naturally occurring enzyme or be recombinantly engineered to express the enzyme) or have exogenous (e.g., by injection, absorption or the like) enzyme capable of cleaving the cleavable linker. Suitable enzymes for cleavage include) for example, use of a KEX2 protease recognition site (Lys, Arg) inserted between glucoamylase and the desired polypeptide to allow in vivo release of the desired polypeptide from the fusion protein as a result of the action of a native *Aspergillus* KEX2-like protease. (Contreras et al., 1991; Broekhuijsen et al., 1993; Ward et al., 1995). Another example of a cleavable linker peptide comprises the recognition sequence Asp-Asp-Asp-Asp-Lys (SEQ ID NO:14), and wherein said fusion protein is cleavable by enterokinase.

Alternatively, the linker may be biodegradable such that the compound of interest is detached from the fusion MPP and compound of interest by hydrolysis and/or enzymatic cleavage inside cells. For example, tumors often express specific proteases, and be used in the delivery of prodrugs of cytotoxic agents. The linker may be selective for lysosomal proteases, such as cathepsin B, C, or D. Delivery of prodrugs and their subsequent activation is well recognized, and such an approach provides significantly less systemic toxicity due to premature linker hydrolysis in the blood, consequently a greater amount of compound of interest, i.e., drug or cytotoxic agent, is delivered to the tumor site. See for example, T. Higuchi and V. Stella provide a thorough discussion of the prodrug concept in Pro-drugs as Novel Delivery Systems, Vol. 14 of the A.C.S. Symposium Series, American Chemical Society (1975). Examples of readily-cleavable groups include acetyl, trimethylacetyl, butanoyl, methyl succinoyl, t-butyl succinoyl, ethoxycarbonyl, methoxycarbonyl, benzoyl, 3-aminocyclohexylidenyl, and the like.

The compound of interest is any organic molecule, and includes small organic molecules, peptides, lipoproteins, and other modified proteins, polysaccharides, oligonucleotides, antisense oligonucleotides, and any other compound thought to have pharmaceutical, prophylactic, diagnostic properties and/or research interest. The compound of interest may be a small organic molecule already known to have pharmaceutical properties, and thus the present invention may be used as a method of treating a patient with the compound of interest. Alternatively, the compound of interest may be a novel protein of unknown function, and thus the present invention may be used as a method of identifying the function of the compound of interest. In another embodiment, the compound of interest may be an antisense molecule, and thus the present invention may be used as a method of altering transcription. In yet another embodiment, the compound of interest may be a prodrug, e.g. in an inactive form but capable of being activated once within the cell. In another embodiment, the compound of interest may be a cytotoxic agent, and thus the invention may be used as a method of delivering a cytotoxic agent to a cell. The compound of interest also includes detectable proteins which are useful to generate conjugated MMP and the detectable protein for identification of new MMPs.

Detectable proteins include GFP, beta galactosidase, radiolabeled proteins and biotinylated proteins, proteins capable of conferring a detectable phenotype in the cell.

The present invention may be used to deliver the compound of interest into a cell in vitro, ex vivo or in vivo. For example, delivery may be carried out in vitro by adding the conjugated MPP and compound of interest extracellularly to cultured cells. Delivery may be carried out ex vivo by adding the conjugated MPP and compound of interest extracellularly or exogenously to a cultured sample removed from a patient, for example, blood, tissue or bone marrow, and returning the treated sample to the patient. Delivery may be carried out in vivo by administering the conjugated MPP and compound of interest by transdermal administration, inhilation, or injection to a patient.

Any type of cell may used in the present invention. The cell may be of mammalian, bacterial, viral or yeast origin. The cell may be a cultured cell such as commonly used for oncology screening. Examples of cultured cells include CHO, HEK293T, HeLa, and NIH3T3. The cell may be a cultured cell from a patient suitable for ex vivo treatment with an MPP conjugate and reintroduction into a patient. The cell may be from the same or different patient than the patient to be treated.

Compositions of the invention comprising the conjugated MPP and compound of interest may be used for therapeutic, prophylactic, diagnostic or research purposes. Compositions may further comprise adjuvants, stabilizers and the like to improve the handling, stability and storage properties of the compositions.

Methods to identify novel MPPs are also pail of the present invention. One method for identification of a membrane penetrating peptide is to generate a conjugate peptide comprising the sequence-$(X-X-X-X)_n$-(SEQ ID NO:54) where n is an integer 1 to 7, and N each time is independently selected from the group consisting of arginine, histidine or lysine, with a detectable protein such as GFP, beta galactosidase and the like, adding the conjugate peptide to a cell and determining if the conjugated peptide is located within the cytoplasm and/or nucleus of the cell. Another method for identification of a membrane penetrating peptide is to generate a conjugate peptide comprising a peptide derived from or overlap ping with a nuclear localization sequence of a mammalian or yeast protein and a detectable protein such as GFP, beta galactosidase and the like, adding the conjugate peptide to a cell and determining if the conjugated peptide is located within the cytoplasm and/or nucleus of the cell.

The following abbreviations are used for amino acids:
A refers to Ala, or alanine;
C refers to Cys or cysteine;
D refers to Asp or aspartic acid;
E refers to Glu or glutamic acid;
F refers to Phe or phenylalanine;
G refers to Gly or glycine;
H refers to His or histidine;
I refers to Ile or isoleucine;
K refers to Lys or lysine;
L refers to Leu or leucine;
M refers to Met or methionine;
N refers to Asn or asparagine;
P refers to Pro or proline;
Q refers to Gln or glutamine;
R refers to Arg or arginine;
S refers to Ser or serine;
T refers to Thr or threonine;
V refers to Val or valine;
W refers to Trp or tryptophan;
Y refers to Tyr or tyrosine.

Proteins are written with the N-terminus to the left.

The following abbreviations are used: 'v/v' refers to volume to volume; 'EYFP' refers to a peptide fragment of the sequence Glu-Tyr-Phe-Pro (SEQ ID NO: 15); 'ORF' refers to Open Reading Frame: 'PCR' refers to polymerase chain reaction; 'CHO' refers to Chinese Hamster Ovary cells; 'HEK293T' refers to Human Embryonic Kidney cells, 'HeLa' refers to epithelial adenocarcinoma cells: 'NIH3T3' refers to Swiss mouse embryo fibroblast cells: 'DMSO' refers to dimethyl sulfoxide; 'FCS' refers to fetal calf serum; 'DMEM' refers to Dulbecco's Modified Eagle's Medium; 'PBS' refers to Phosphate buffered saline; 'BSA' refers to bovine serum albumin; 'C-terminus' refers to the carboxy-terminus; 'N-terminus' refers to the amino-terminus; 'PTD' refers to Peptide transduction domain; 'GPCR' refers to G-protein coupled receptor; 'TM' refers to a transmembrane domain of a GPCR; 'I' refers to an intracellular loop of a GPCR; '5HT2A' refers to serotonin receptor 2A; and 'mAb' refers to monoclonal antibody.

EXAMPLES

Example 1

Identification of an NLS within hPER1

Plasmid Construction

All hPer1 fragments described here are cloned as in-frame C-terminal fusion to EYFP. EYFP-hPer1 ORF, P1-N and P1-NX (FIG. 1A) is generated by insertion of EcoRI and XhoI digested fragments into EYFP-C1 vector (Clontech). The other fragments are PCR amplified from the full-length hPer1 cDNA and subcloned into EYFP-C1 vector. The first and the last residue present in each of fragment is indicated in FIG. 1A. All constructs are verified by automated DNA sequencing.

Cell Culture and DNA Transfection

CHO, HeLa and 293T cells are maintained in Dulbecco's Modified Eagle's Medium (DMEM) supplemented with 10% fetal calf serum (FCS), 50 units/ml penicillin, 50 µg streptomycin, and 4 mM L-glutamine (hereafter referred to as complete DMEM) at 37° C. with 5% $CO_2$. Transfection of the cells is carried in two-well Lab-Tek coverslips (Nunc Inc.) with LIPOFECT-AMINETM™ Reagent (Life Technologies) according to the manufacturer's instructions.

Peptides and Peptide Internalization

Peptides are synthesized by a commercial vendor (Bio Synthesis). For peptides internalization, cells are plated into two-well Lab-Tek coverslips (Nunc Inc.) at a density of $2 \times 10^5$ cells/well and cultured overnight. The peptides are dissolved in DMSO diluted to indicated concentration with PBS. The cell monolayers were incubated with the appropriate peptide/PBS solution at 1 µM standard concentration for 10 min at room temperature (RT) unless otherwise specified. For experiments at 4° C., the protocol was the same except that all incubations were performed at 4° C. until the end of the fixation procedure.

Immunofluorescence and Microscopy

For direct detection of expression and subcellular localization of EYFP fusion protein, transfected cells were examined directly without fixation or after fixation with 4% (v/v) formaldehyde in PBS for 20 min at 4° C. and washed with PBS. For indirect immunodetection of biotinylated peptides, fixed cell were washed twice with PBS and permeabilized with 0.3% Triton X-100 in PBS for 20 min at 4° C. and blocked with 2%

BSA in PBS for 30 min at RT. Cells were then washed with PBS and incubated with Streptavidin-FITC™ (Sigma) or Alex499 (Molecular Probe), 1:400 diluted in 0.2% Tween 20, 2% BSA in PBS for 1 h at RT. Following 2×5 min washes with PBS and once with 0.3% Triton X-100 in PBS for 20 min RT. In some experiment, the nucleus was stained with 50 ng/ml Hoechst 33258 (Sigma) or 3 µg/ml propidium iodide in PBS. The subcellular localization of the fluorescence was analyzed on an Olympus microscope. Confocal images were taken on a Zeiss confocal laser scan microscope (CLSM phoibos 1000).

Though it is known that nuclear entry of PER1 is important for its function, no putative NLS was identified using a standard Profile Scanning program (Shearman, L. P., et al., *Neuron* 19, 1261-1269 (1997), Yagita, K., et al., *Genes Dev.* 14, 1353-1363 (2000)). To determine the NLS of hPER1 experimentally, three full-length hPER1 (P1-FL) were constructed and denoted as P1-N, P1-NM and P1-C (FIG. 1A). The ability of these constructs to localize to the nucleus in CHO cells then analyzed. An EYFP-tag was used to facilitate the detection of hPER1 in living cells; however, the EYEP-tag had no apparent contribution on hPER1 fusion protein localization since hPER1 constructs made with an N-terminal Flag-tag presented an identical cytological distribution pattern (data not shown). After transient transfection, both P1-FL and P1-NM proteins were expressed in the nucleus of transfected cells as early as 10 hours post-transfection, while both P1-N and P1-C accumulated only in the cytoplasm (FIG. 1B). The EYFP vector control was diffuse in both the nucleus and cytoplasm. These results demonstrate that a functional NLS in hPER1 is located between P1-N and P1-C in what we designated as region M (see FIG. 1A).

To further localize the NLS in region M (amino acids 481-890), a series of 8 deletion constructs, P1-F1 to P1-F8, were generated and the subcellular distribution of each mutant was assayed as indicated in FIGS. 1A and B. Sequential deletion from amino acid 581 (P1-F2) to position 821 (P1-F7) of region M resulted in nuclear localization. Further deletion of amino acids 821 to 841 (P1-F8) resulted in a diffused fluorescent pattern within transfected cells with a localization pattern similar to that of the EYFP vector control.

These data indicate that a NLS exists between amino acids 821 and 890, and is located at the C-terminus of region M. This observation was confirmed by the construction of an additional EYFP fusion protein, P1-NLS, which contained hPER1 amino acids 830-845. This region contains a string of basic residues that might function as a NLS (Weis, K., *Trends Biochem. Sci.* 23, 185-189 (1998), Truant, R. and Cullen, B. R. *Mol Cell Biol.* 19, 1210-1217 (1999)). As expected, P1-NLS exhibited nuclear localization in 100% of transfected cells (FIG. 1B). Other regions of PER1 in additional fusion constructs failed to localize to the nucleus (data not shown). Therefore, we conclude that the NLS of hPER1 (hPER1-NLS) is localized to within amino acids 830-845. Interestingly, construct P1-F1 has a strictly cytoplasmic localization pattern irrespective of the fact that it contains the NLS, supporting published observations that this region also contains and as yet unidentified cytoplasmic localization domain (Vielhaver, E., et al., *Mol Cell Biol.* 20, 4888-4899 (2000)). Sequence alignment shows that the hPER1-NLS is conserved between human and mouse PER1 proteins (FIG. 1A), but not with other putative NLSs, or with other human, mouse or *Drosophila* PERs. After completion of our studies, Vielhaber et al. (2000), identified a longer mouse PER1-NLS that contains our identified 16 amino acid sequence (Vielhaver, E., et al., *Mol Cell Biol.* 20, 4888-4899 (2000)); thus, supporting our findings.

Example 2 hPER1-NLS Encodes an MPP

Two common features of the three identified gene encoded MPPs (TAT, Antp, and VP22) are that they are derived from nuclear proteins and they consist of basic amino acid residues (Lindgren. M., et al., *Trends Pharmacol Sci.* 3, 99-103 (2000)). hPER1 is also a nuclear protein whose NLS is rich in basic amino acids (SRRHHCRSKAKRSRHH (SEQ ID NO:16), see FIG. 1). These similarities led us to determine whether hPER-NLS might also function as a MPP. In order to test this hypothesis, we synthesized several N-terminally biotinylated peptides: hPER1-MPP, Flag-tagged hPER1-MPP, Flag-tagged TAT-PTD, Flag-Flag alone, See Table 1 below:

TABLE 1

| Name | Amino Acid Sequence | Transducing Peptide[1] | Nuclear Localization Fusion Protein[2] |
|---|---|---|---|
| HPER1 | GRRHHCRSKAKRSRHH (SEQ ID NO:17) | + | + |
| Flag-hPER1 | GMDYKDDDDKGSRRHHCRSKAKRSHH (SEQ ID NO:18) | + | nd |
| Flag-TAT | GMDYKDDDDKGYGRKKKRRQRRR (SEQ ID NO:19) | + | + |
| Flag | GMDYKDDDDKGMDYKDDDDK (SEQ ID NO:20) | − | − |
| Antennapedia | GRQIKIWFQNRRMKWKK (SEQ ID NO:21) | + | nd |
| 9 Arginine | GPRRRRRRRR (SEQ ID NO:22) | + | nd |

TABLE 1-continued

| Name | Amino Acid Sequence | Transducing Peptide[1] | Nuclear Localization Fusion Protein[2] |
|---|---|---|---|
| 9 Lysine | GKKKKKKKKK (SEQ ID NO:23) | + | nd |
| 9 Histidine | GHHHHHHHHH (SEQ ID NO:24) | − | nd |
| NLSs: | | | |
| SV40 | GDPKKKRKV (SEQ ID NO:25) | − | + |
| hPER2 | GKKTGKNRKLKSKRVKPRD (SEQ ID NO:26) | − | + |
| hPER3 | GRKGKHKRKKLP (SEQ ID NO:27) | + | + |
| Thyroid A-1 | GKRVAKRKLIEQNRERRR (SEQ ID NO:28) | + | + |
| HME-1 | GRKLKKKKNEKEDKRPRT (SEQ ID NO:29) | + | + |
| ABL-1 | GKKTNLFSALIKKKKTA (SEQ ID NO:30) | + | + |
| Nucleoplasmin X | GRRERNKMAAAKCRNRRR (SEQ ID NO:31) | + | + |
| C-FOS | GRRERNKMAAAKCRNRRR (SEQ ID NO:31) | − | + |
| GCN-4 | GKRARNTEAARRSRARKL (SEQ ID NO:32) | + | + |
| [R/H/K]- | | | |
| [R/H/K]- | | | |
| [R/H/K]- | | | |
| [R/H/K] | | | |
| HEN1/NSLC1 | GRRRRATAKYRTAH (SEQ ID NO:33) | + | + |
| HEN2/NSLC2 | GKRRRATAKYRSAH (SEQ ID NO:34) | + | + |
| HNF3 | GRRRRKRLSHRT (SEQ ID NO:35) | + | + |
| cAMP dependent TF | GRRRRRERNK (SEQ ID NO:36) | + | + |
| Cyclin L ania-6a | GKHRHERGHHRDRRER (SEQ ID NO:37) | − | + |
| beta Zip TF | GKKKRKLSNRESAKRSR (SEQ ID NO:38) | − | + |
| GFP | | nd | − |

Fn 1: Results shown for selected MPPs, see FIG 5
Fn 2: Results shown for selected MPPs, see FIG 5

Figure 2:
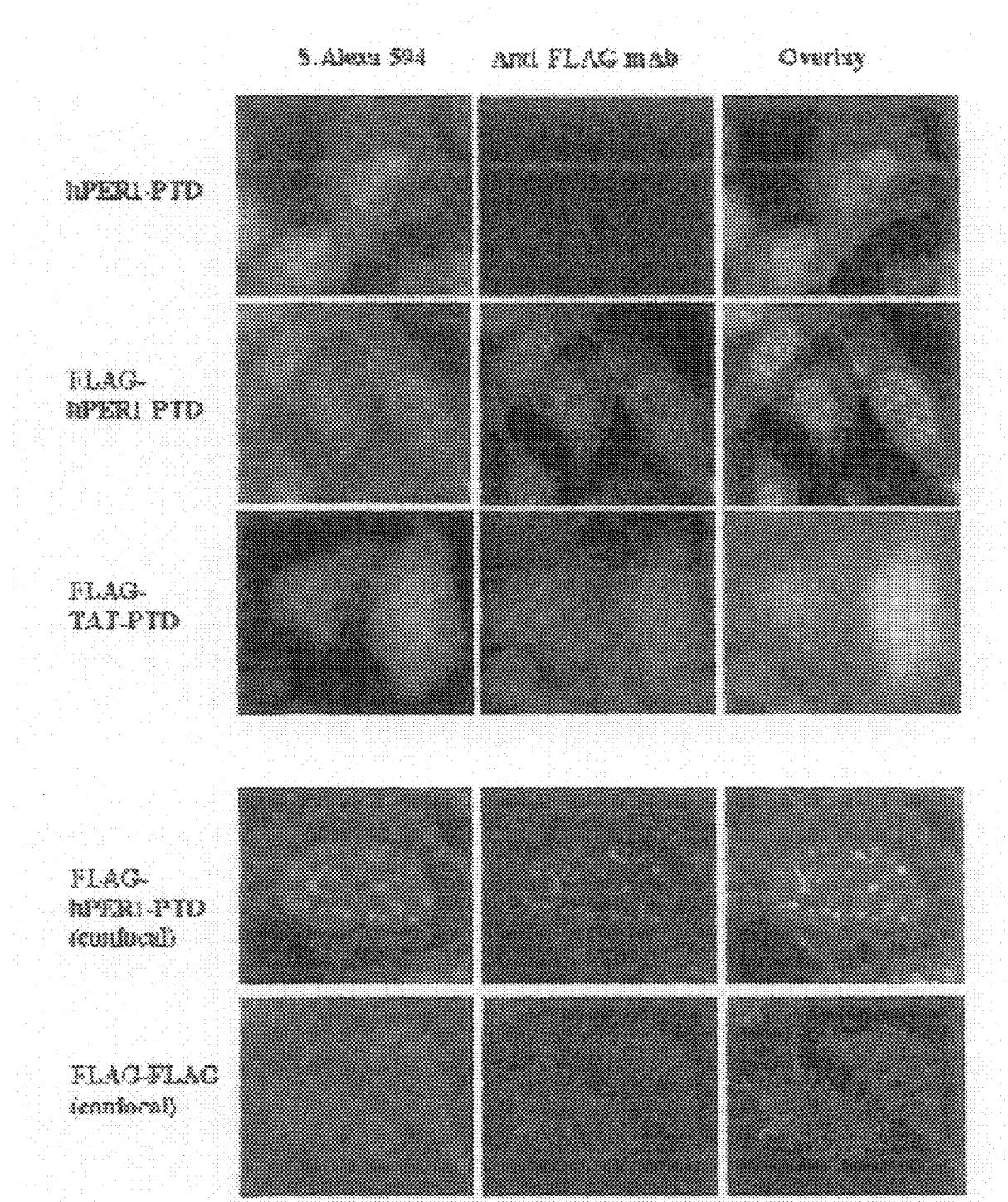
FIG. 2. Membrane penetration assay in CHO cells. N-terminal biotinylated synthetic peptides hPER1-PTD, Flag-hPER1-PTD, Flag-TAT-PTD (positive control), and Flag-Flag (negative control) were assayed for their ability to penetrate cellular membranes in living CHO cells in culture. The subcellular localization of internalized peptides was determined using a two color staining method, either Streptavidin-Alexa 594 (red) or anti-flag mAb. The third column is an overlay. Confocal microscopy was employed to further confirm intracellular and intranuclear localization. Single section of confocal imaging is shown.
Figure 5A:
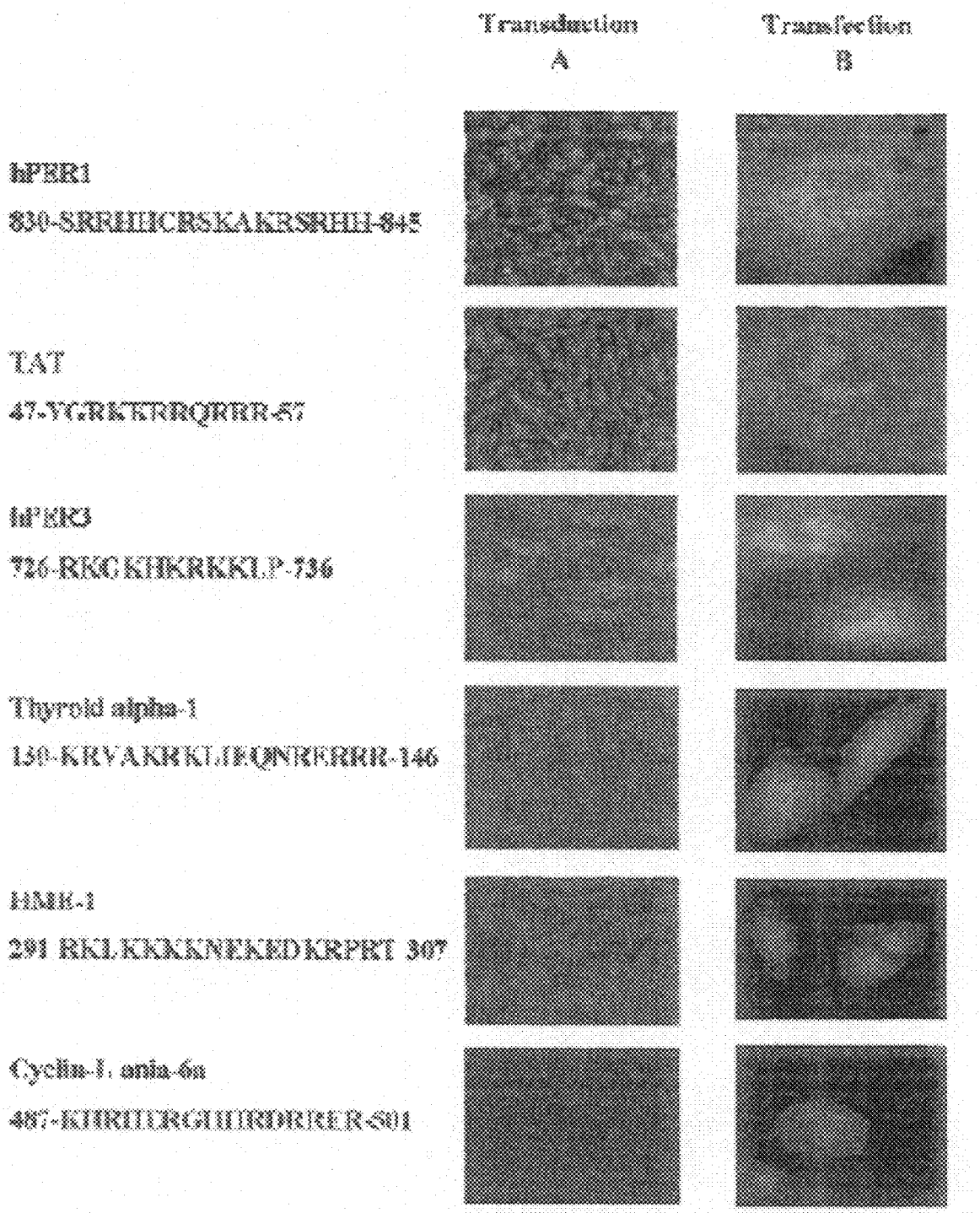
FIGS. 5 (A and B) Identification of additional PTDs. Putative PTD sequences were searched using a combined bioinformatics method that included SwissPro, PRF, PIR-Protein info Resource, PDB with peptides sequences translated from the annotated protein coding region n GenBank with "transcription factor" as the key word. We initially searched for all known or putative NLS's. Secondly, we employed the PHI-BLAST (Pattern-Hit Initiate BLAST) to search for the degenerative pattern occurrence [R/H/K]-[R/H/K]-[R/H/K]-[R/H/K], (X)n where n is an integer of 4 or larger and X each time is independently selected to be either arginine, histidine, or lysine. 7374 putative PTD sequences were identified. From the two searches we synthesized (A) biotinylated peptides to these sequences or (B) created in frame fusion proteins with GFP and transfected CHO cells. 9 of the 12 peptides were found to transduce, and all sequences localize to the nucleus in transfected cells. hPER1-PTD, hPER3-PTD, and TAT-PTD peptides were used as positive controls. Six positive sequences and 2 negative sequences are shown. Numbers represent the amino acid residues within the parental protein sequence and Gene bank accession numbers for these proteins are indicated as follows: (M24899, human Thyroid hormone alpha-1; L12699, human Homeobox protein Engrailed 1 HME1; X16416, human Proto-oncogene tyrosine protein kinase ABL1; Q02575, human HEN1/NSL1; Q02577, human HEN2/NSLC2; AAA74561, rat HNF-3: CAB65887, Drosophila cAMP dependent transcription factor). Three negative peptides are (V01512, c-Fos; AAD53184, human cyclin L ania-6a; CAB66914, Arabidopsis .beta.-zip transcription factor).
Figure 5B:
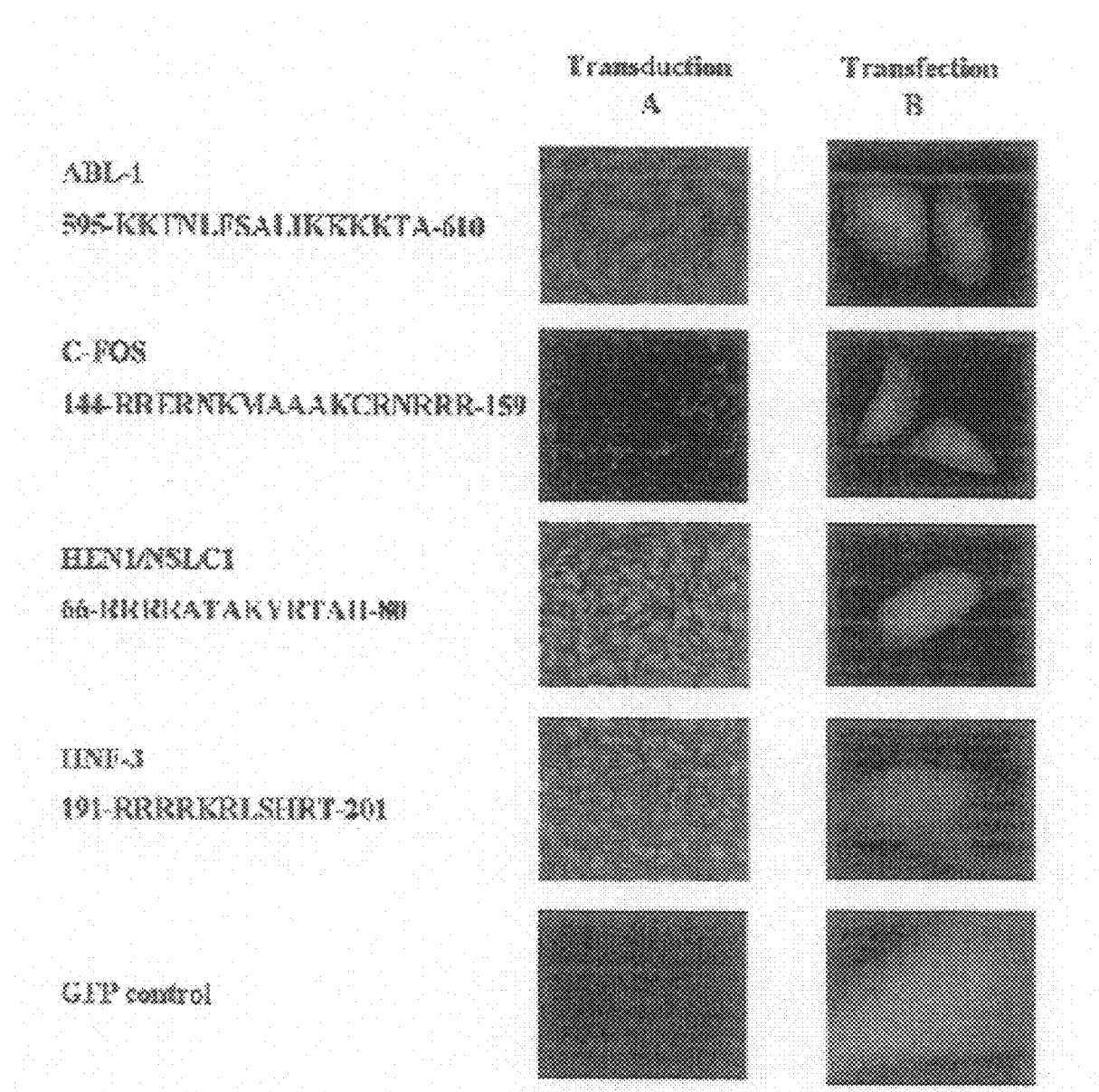

The peptides are assayed for their ability to penetrate cellular membranes. Intracellular localization is assayed by direct staining with labeled Streptavidin ALEXA reagents or by indirect staining with anti-Flag mAb followed by the addition of labeled secondary antibodies. When added to the cells in culture at a concentration of 10 μM, hPER1-MPP, Flag-hPER1-MPP and Flag TAT-PTD peptides are found to penetrate rapidly into 100% cells (FIG. 2 and FIG. 5). By both detection methods, hPER1-MPP, Flag-tagged hPER1-MPP, and Flag-tagged TAT-PTD are observed to be diffusely distributed throughout the cytoplasm, but concentrated within subnuclear domains that appear as distinct foci within the nucleoplasm and the nucleolus. In contrast, biotinylated negative control peptides, Flag-Flag and several additional peptides derived from other hPER1 regions are only barely discernible background staining, with no staining in the nucleus or nucleoli, even at high concentrations (data not shown). Confocal microscopy is used to confirm the intracellular and intranuclear staining of Flag-tagged hPER1-MPP, and that the negative control peptides are not internalized (FIG. 2).

hPER1-MPP rapidly penetrated the cellular membranes and localized in nuclear regions with efficiencies similar to the TAT-PTD peptide. Identical results are obtained using CHO, HEK293T, HeLa, NIH3T3 and cultured rat primary cortical neurons (data not shown), indicating cell type-independent penetration.

hPER1-MPP internalization occurs rapidly (within 5 min), with similar potencies at 4 C and 37 C and even after cell membrane fixation (data not shown). Thus, the amino acid sequence 830-845 of hPER1 functions as both as a protein nuclear/nucleolar localization signal in the fusion protein and as a MPP, and that membrane penetration is independent of traditional receptor-mediated endocytic mechanisms.

Example 3

Arginine 7 is Essential for hPER1-MPP Activity

To date, the mechanisms as well as the structural basis whereby MPPs transverse cellular membranes have not been elucidated. We therefore sought to determine if there were key residues within hPER1-MPP that were important for maintaining those properties essential for its membrane penetrating potential. We separately replaced each amino acid in hPER1-MPP to alanine (Table 2), and assayed for the ability of these mutated peptides to penetrate living cells relative to the wild-type hPER1-MPP.

| Name | hPER1-PTD alanine substitution | Transducing Peptide |
|---|---|---|
| hPER1-PTD | S R R H H C R S K A K R S R H H (SEQ ID NO:39) | + |
| R2A | S A R H H C R S K A K R S R H H (SEQ ID NO:40) | + |
| R3A | S R A H H C R S K A K R S R H H (SEQ ID NO:41) | + |
| H4A | S R R A H C R S K A K R S R H H (SEQ ID NO:42) | + |
| H5A | S R R H A C R S K A K R S R H H (SEQ ID NO:43) | + |
| C6A | S R R H H A R S K A K R S R H H (SEQ ID NO:44) | + |
| R7A | S R R H H C A S K A K R S R H H (SEQ ID NO:45) | - |
| S8A | S R R H H C R A K A K R S R H H (SEQ ID NO:46) | + |
| K9A | S R R H H C R S A A K R S R H H (SEQ ID NO:47) | + |
| K11A | S R R H H C R S K A A R S R H H (SEQ ID NO:48) | + |
| R12A | S R R H H C R S K A K A S R H H (SEQ ID NO:49) | + |
| S13A | S R R H H C R S K A K R A R H H (SEQ ID NO:50) | + |
| R14A | S R R H H C R S K A K R S A H H (SEQ ID NO:51) | + |
| hPER1-PTD13 | R R H H C R S K A K R S R (SEQ ID NO:52) | + |
| hPER1-Control (484-503) | Q E L S E Q I H R L L L Q P V (SEQ ID NO:53) | - |

Figure 3:
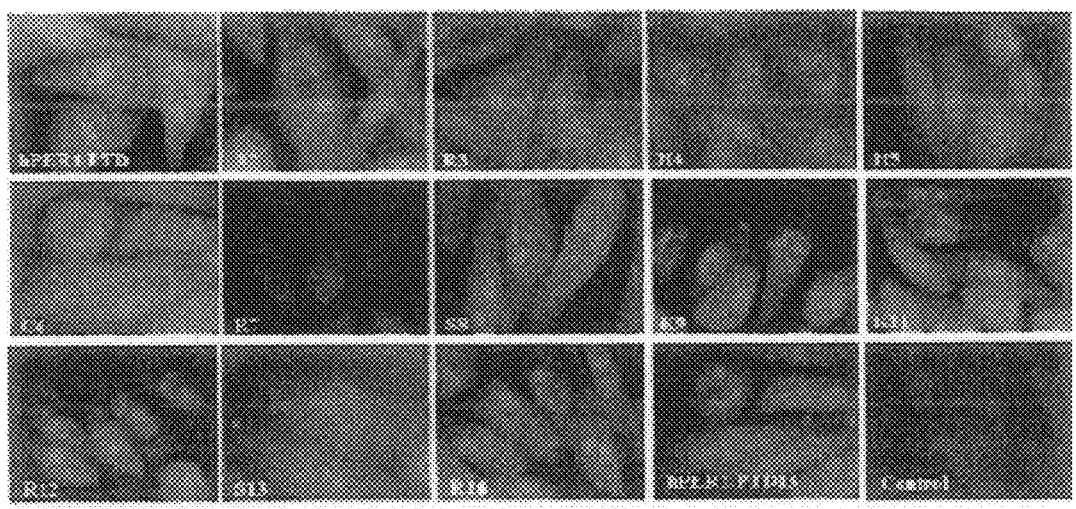
FIG. 3. Alanine scanning of hPER1-PDTs. Biotinylated hPER1-NPDs were synthesized with a single amino acid residue substitution at the indicated position with an alanine and assayed for membrane penetration in CHO cells. Cells were incubated for 10 minutes at 37 C. at a peptide concentration of 10 µM followed by washing, fixation, permeablization, and then detected with labeled Streptavidin Alexa-594 (red, 2 µg/ml) for 15 minutes at the RT. Control peptide was from hPER1 N-terminal amino acids residues 486-500.

As shown in FIG. 3, most of the single alanine substitutions had very little effect on membrane penetrating capabilities as compared with wild-type peptide. However, changing arginine 7 to an alanine (R7A) reduced the detectable cytological signal to that observed for the negative control peptides. Thus, the arginine 7 to alanine mutation significantly reduced the membrane penetrating properties of hPER1-MPP. Identical observations were observed after changing arginine 7 to glutamic acid (R7E) (data not shown). Furthermore, the simultaneous deletion of the N-terminal serine and of the two C-terminal histidine from hPER1-MPP (hPER1-MPP13) had little overall effect on the positive membrane penetrating potential of the peptide (FIG. 3).

The arginine 7 residue plays a critical role in the cell penetrating ability of the hPER1-MPP. We therefore sought to determine if the R7A mutation affected nuclear translocation of a fusion protein P1-NLS. CHO cells transfected with fusion protein P1-R7A (arginine 7 mutated to alanine) have intense nuclear staining similar to the wild-type, P1-NLS (data not shown). Nuclear translocation appears to be normal in the P1-R7A mutant fusion protein, but subnuclear targeting to the nucleoli is disrupted (data not shown). These data indicate that membrane penetration and nucleoli targeting are affected by the single R7 amino acid residue and indicate that nuclear translocation of hPER1-NLS has separate and distinct determinants.

Example 4 hPER1-MPP Delivery of Functioning Molecules

Figure 4A:
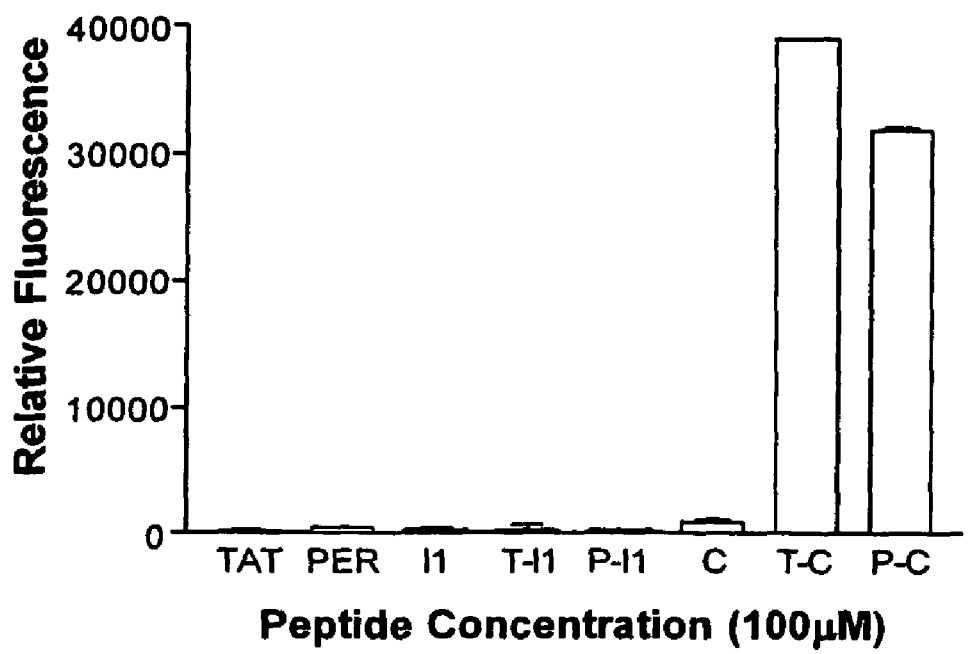
FIG. 4. Activation of serotonin 5HT2A receptor with hPER1-MPP fusion peptide. (A). hPER1-MPP and TAT-PTD peptides were synthesized alone or in fusion with either the first intracellular loop I1 (SLEKKLQNATN (SEQ ID NO:10)), or the C-terminal Transmembrane 7 domain. TM7 (KTYRSAFSRYIQYKENKKPLQLI (SEQ ID NO:11) derived from the 5HT2A receptor, genebank accession number, M86841). Receptor activities was assayed using standard FLIPR analysis and measuring endogenous and exogenous $Ca^{+2}$ levels. Peptide designations are as follows: T (TAT-PTD), P (hPER1-MPP), I1 (intracellular loop 1), T-I1 (TAT-PTD-I1), P-I1 (hPER1-MPP-I1), TM7 (C-terminal domain), TTM7 (TAT-PTD-TM7), PTM7 (hPER1-MPP-TM7), and S (Serotonin).
Figure 4B:
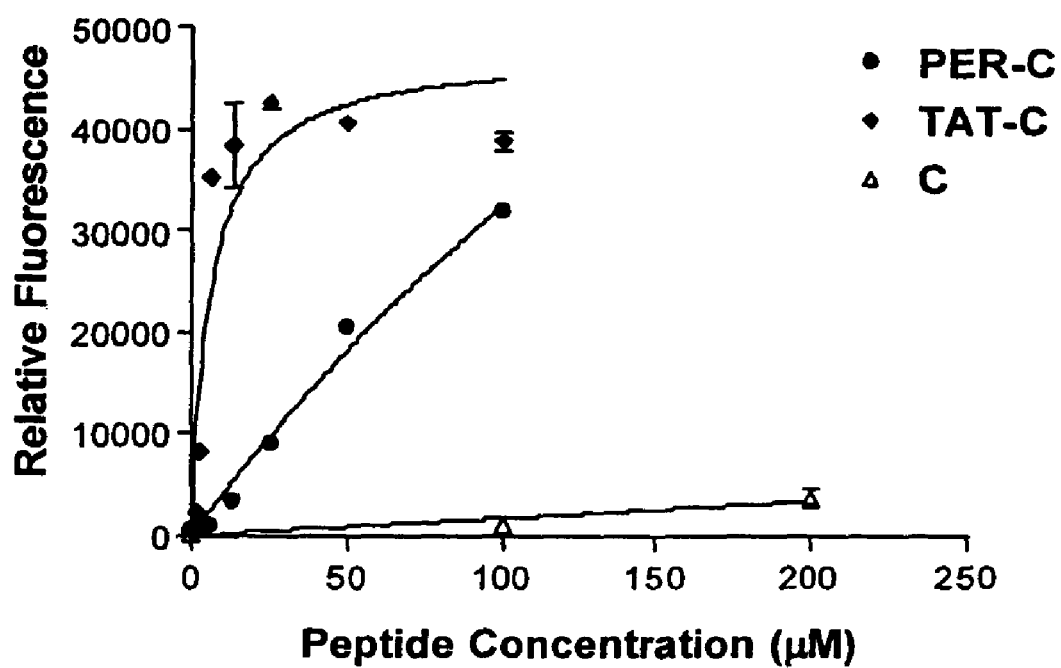

One of the features of MPPs is their ability to cargo proteins and peptides into cells. We were successful in coupling hPER1-MPP to B-galactosidase and in delivering the fusion protein into cells in culture (data not shown), as has been described by Fawells et al., 1994 (Fawell, S., et al., *Proc Natl Acad Sci USA*. 91, 664-668 (1994)). However, to further extend the functional utility of MPPs, we tested hPER1-MPP in fusion with a physiologically relevant and biologically active peptide. Wess and collegues (1993) have shown a functional role for the conserved transmembrane segment 7 (TM7) of the G-protein coupled receptor (GPCR) superfamily. Along with TM7, the third intracellular loop (I3) plays a significant role in GPCR calcium signaling (Wess, J M., et al., *EMBO J*. 12, 331-338 (1993)) while intracellular loops 1 and 2 (I1 and I2) appear not to be important. Using the serotonin receptor, 5HT2A, we experimentally tested the ability of hPER1-MPP and TAT-PTD in fusion with peptides designed from I1 and the TM7 domains to activate the receptor. Biotinylated peptides hPER1-MPP TM7, TAT-PTD TM7, hPER1-MPP I1, TAT-PTD I1, hPER-MPP, TAT-PTD, TM7 or I1 were incubated at a concentration of 10 µM with a 5HT2A receptor CHO stable cell line. Peptide membrane penetration was assayed using Streptavidin-Alexa 594 as described above. As shown in FIG. 4A, receptor signaling is activated by the addition of exogenous serotonin, hPER1-MPP TM7, and TAT-PTD TM7 as measured by the level of the calcium response. However, TM7 alone nor any of the other peptides were able to generate a calcium response. Furthermore, the activation of the receptor by hPER1-MPP TM7 and TAT-PTD TM7 is peptide concentration dependent, FIG. 4B. The addition of increasing concentrations of the activating peptide, TM7, in fusion with hPER1-MPP or TAT-PTD results in a calcium response in a dose dependent manner. TAT-PTD TM7 appears to be a more potent 5HT2A receptor activator than is hPER1-MPP TM7. A simple explanation for this result is that TAT-PTD TM7 is more cytoplasmically localized or has greater cell penetrating capabilities than hPER1-MPP TM7, although we have not observed that to be the case. Similar results were also obtained in this laboratory using hPER1-MPP in fusion with p-adrenergic activating peptides (unpublished data). These data support previous results that hPER1-MPP not only penetrates cell membranes, but also demonstrates that it is capable of cargoing peptides to intracellular compartments to initiate biologically relevant signal transduction events.

Example 5

Identification of Other Gene Encoded MPPs

Since hPER1 is a nuclear protein proposed to be involved in transcriptional regulation, and since, to date, all PTDs derived from naturally occurring proteins are transcription factors (TAT, Antp, and VP22), we sought to determine if other PTD sequences existed within the genome. To this end, we used two approaches; first, we searched the NCBI non-redundant protein database for all known and putative NLS's (table 1, 10-17). We synthesized peptides corresponding to the NLS amino acid sequences and assayed for peptide transduction. As shown in table 1 and FIG. 5, 6 of the 7 peptides synthesized had membrane penetrating characteristics similar to hPER-PTD and TAT-PTD. These proteins included human proteins of the thyroid hormone receptor alpha-1, homeobox protein HME1, and proto-oncogene protein ABL-1. Furthermore, (table 1 and FIG. 5) when we create in frame fusion proteins between these peptide sequences and GFP then transfected into CHO or HEK 293T cells, all of the sequences conferred nuclear localization of the fusion protein.

Our second approach to identifying PTDs involved searching the NCBI non-redundant protein database collection with a degenerative algorithm (see FIG. 5, legend). Using these search parameters, we found 533,291 sequences of which the conditions for the algorithm were satisfied 129,169 times (24%). By limiting our search to include either "transcription factors, cytokines or tyrosine kinases", we identified 8280 transcription factor protein sequences of which the algorithm pattern occurred 7374 times (89%); within 2333 cytokine protein sequences the pattern occurred 450 times (19%); and within 2513 tyrosine kinase protein sequences the pattern occurred 843 times (36%). Because the algorithm occurred most frequently in nuclear proteins, we synthesized peptides to putative PTDs for 6 of the "transcription factor" sequences and assayed for their ability to penetrate into the cells. As shown in table 1, results in lines 18-23 and FIG. 3A, 4 of the 6 peptides tested had membrane penetrating properties similar to hPER1-PTD and TAT-PTD. These proteins included two human proteins HEN1/NSLC-1 and HEN2/NSLC-2 which are reported to be involved in neuronal differentiation and development (Uittenbogaard, M., Peavy, D. R. and Chiaramello, A. 1999. Expression of the bHLH gene NSCL-1 suggests a role in regulation of cerebellar granule cell growth and differentiation. *J. Neurosci. Res*. 57:770-781, Lipkowitz, S. et al. 1992. A comparative structural characterization of the human NSCL-1 and NSCL-2 genes. Two basic helix-loop-helix genes expressed in the developing nervous system. *J. Biol. Chem*. 267:21065-21071), rat HNF-3 (17), and a *Drosophila* cAMP dependent transcription factor (18). Furthermore, (table 1 and FIG. 5) when we create in frame fusion proteins between these peptides and GFP and transfected into CHO or HEK 293T cells, all of the sequences conferred nuclear localization of the fusion protein. These results indicate that PTD sequences can be found within or overlapping with NLSs. However not all NLSs are PTDs as is apparent in SV40, hPER2, C-FOS, Cyclin L ania-6 and beta Zip transcription factor NLSs (table 1). These results also suggest that PTDs sequences are prevalent throughout the genome and in particular within nuclear proteins.

Example 6 hPER-PTD with β-Galactosidase

Figure 6:
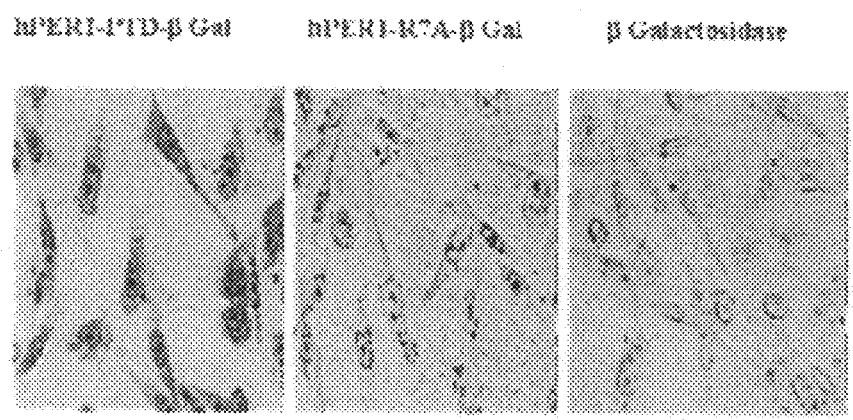
FIG. 6. hPER-PTD cargo's β-Galactosidase into cells: At least one feature of HIV TAT transducing peptide is its ability to cargo proteins into cells and tissues. We therefore sought to determine if hPER1 transducing peptide could cargo beta galactosidase into cells. To perform this experiment, we followed a protocol by Frankel et al. 1989 (19):7397-401, whereby, we chemically linked hPER1-PTD or hPER-PTD R7A to full length β-galactosidase and assayed for the ability of these conjugates and beta-galactosidase protein alone to transduce into CHO cells. As shown in the FIG. 6, left, cells incubated with hPER-PTD β-galactosidase fusion showed positive enzymatic activity for β-galactosidase as indicated by the blue color in the cells after the addition of X-gal. However, neither hPER-MPP R7A β-galactosidase (center) nor β-galactosidase protein (right) alone was able to enter the cells as indicated by a no blue staining reactivity after the addition of X-gal. These data indicate that like TAT peptide, hPER1-PTD can cargo a large (120 kD) protein into cells.

At least one feature of HIV TAT transducing peptide is its ability to cargo proteins into cells and tissues. We therefore sought to determine if hPER1 transducing peptide could cargo beta galactosidase into cells. To perform this experiment, we followed a protocol by Frankel et al. PNAS 1989 (19):7397-401, whereby, we chemically linked hPER1-PTD or hPER-PTD R7A (with Ala replacing Arg[7]) to full length β-galactosidase and assayed for the ability of these conjugates and beta-galactosidase protein alone to transduce into CHO cells. As shown in the FIG. 6, panel 1, cells incubated with hPER-PTD β-galactosidase fusion showed positive enzymatic activity for β-galactosidase as indicated by the blue color in the cells after the addition of X-gal. However, neither hPER-MPP R7A β-galactosidase nor β-galactosidase protein alone was able to enter the cells as indicated by a no blue staining reactivity after the addition of X-gal, panels 2 and 3. These data indicate that like TAT peptide, hPER1-PTD can cargo a large (120 kD) protein into cells.

We claim:

1. A fusion protein for delivery of an organic molecule into a cell comprising a membrane penetrating peptide attached to said organic molecule, wherein the membrane penetrating peptide is not full length human Period 1 protein or full length human Period 3 protein, said membrane penetrating peptide comprising a peptide selected from the group consisting of the peptides: RRHHCRSKAKRSRHH (SEQ ID NO:56), SRRHHCRSKAKRSRHH (SEQ ID NO: 16), SARHHCRSKAKRSRHH (SEQ ID NO:40), SRAHHCRSKAKRSRHH (SEQ ID NO:41), SRRAHCRSKAKRSRHH (SEQ ID NO:42), SRRHACRSKAKRSRHH (SEQ ID NO:43), SRRHHARSKAKRSRHH (SEQ ID NO:44), SRRHHCRAKAKRSRHH (SEQ ID NO:46), SRRHHCRSAAKRSRHH (SEQ ID NO:47), SRRHHCRSKAARSRHH (SEQ ID NO:48), SRRHHCRSKAKASRHH (SEQ ID NO:49), SRRHHCRSKAKRARHH (SEQ ID NO:50), SRRHHCRSKAKRSAHH (SEQ ID NO:51) and RRHHCRSKAKRSR (SEQ ID NO:52) and RKGKHKRKKLP (SEQ ID NO:55).

2. The fusion protein according to claim 1, wherein the membrane penetrating peptide comprises the peptide GRKGKHKRKKLP (SEQ ID NO: 27).

3. The fusion protein according to claim 2, wherein the membrane penetrating peptide comprises a peptide selected from the group consisting of the peptides: SRRHHCRSKAKRSRHH (SEQ ID NO: 16) and GRRHHCRSKAKRSRHH (SEQ ID NO: 17).

4. The fusion protein of claim 1, wherein the organic molecule is directly chemically attached to the membrane penetrating peptide or by a linker.

5. The fusion protein of claim 4, wherein the linker is an amino acid linker or a polypeptide linker.

6. The fusion protein of claim 1, wherein the membrane penetrating protein is produced by recombinant technology, chemical synthesis or degradation of a precursor protein.

7. The fusion protein of claim 1, wherein the organic molecule is a small organic molecule, peptide, protein, lipoprotein, glycoprotein, polysaccharide, oligonucleotide, or antisense oligonucleotide.

8. A fusion protein for delivery of a peptide, protein or glycoprotein into a cell consisting essentially of a membrane penetrating peptide attached to said peptide, protein or glycoprotein, wherein said membrane penetrating peptide comprises a peptide that is selected from the group consisting of human Period 1 nuclear localization sequence RRHHCRSKAKRSRHH (SEQ ID NO:56) and human Period 3 nuclear localization sequence RKGKHKRKKLP (SEQ ID NO:55) wherein the membrane penetrating peptide is not full length human Period 1 protein or full length human Period 3 protein.

9. A fusion protein for delivery of an oligonucleotide into a cell comprising a membrane penetrating peptide attached to said oligonucleotide, wherein said membrane penetrating peptide is selected from the group consisting of the peptides: RRHHCRSKAKRSRHH (SEQ ID NO:56) and RKGKHKRKKILP (SEQ ID NO:55).

10. The fusion protein of claim 5, wherein the linker is a polypeptide linker of five or fewer amino acids.

11. The fusion protein of claim 5, wherein the polypeptide linker is selected from the group consisting of GFLG (SEQ ID NO: 13), GG, GL and G.

12. A purified fusion protein for delivery of a peptide, protein or glycoprotein into a cell comprising a membrane penetrating peptide, said membrane penetrating peptide including a nuclear localization sequence, said membrane penetrating peptide being attached to said peptide, protein or glycoprotein, wherein said nuclear localization sequence of said membrane penetrating peptide comprises a peptide that is selected from the group consisting of human Period 1 nuclear localization sequence RRHHCRSKAKRSRHH (SEQ ID NO:56) and human Period 3 nuclear localization sequence RKGKHKRKKLP (SEQ ID NO:55) wherein the membrane penetrating peptide is not full length human Period 1 protein or full length human Period 3 protein.

* * * * *

UNITED STATES PATENT AND TRADEMARK OFFICE
CERTIFICATE OF CORRECTION

PATENT NO. : 7,754,678 B2
APPLICATION NO. : 11/251734
DATED : July 13, 2010
INVENTOR(S) : Yong Guo et al.

Page 1 of 1

It is certified that error appears in the above-identified patent and that said Letters Patent is hereby corrected as shown below:

In column 48, line 19-20, in claim 9, delete "RKGKHKRKKILP" and insert -- RKGKHKRKKLP --, therefor.

Signed and Sealed this
Fifth Day of April, 2011

David J. Kappos
*Director of the United States Patent and Trademark Office*